United States Patent
Dong et al.

(10) Patent No.: US 8,450,266 B2
(45) Date of Patent: May 28, 2013

(54) ANALOGUES OF GLUCOSE-DEPENDENT INSULINOTROPIC POLYPEPTIDE

(75) Inventors: Zheng Xin Dong, Holliston, MA (US); Yeelana Shen, Franklin, MA (US); Daniel B. DeOliveira, Bellingham, MA (US)

(73) Assignee: Ipsen Pharma S.A.S., Boulogne Billancourt (FR)

( * ) Notice: Subject to any disclaimer, the term of this patent is extended or adjusted under 35 U.S.C. 154(b) by 17 days.

(21) Appl. No.: 13/057,864

(22) PCT Filed: Aug. 7, 2009

(86) PCT No.: PCT/US2009/004543
§ 371 (c)(1),
(2), (4) Date: Feb. 12, 2011

(87) PCT Pub. No.: WO2010/016935
PCT Pub. Date: Feb. 11, 2010

(65) Prior Publication Data
US 2011/0136724 A1    Jun. 9, 2011

Related U.S. Application Data

(60) Provisional application No. 61/188,192, filed on Aug. 7, 2008, provisional application No. 61/200,628, filed on Dec. 2, 2008.

(51) Int. Cl.
*A61K 38/00* (2006.01)
(52) U.S. Cl.
USPC ................................................ 514/1.1
(58) Field of Classification Search
None
See application file for complete search history.

(56) References Cited

U.S. PATENT DOCUMENTS

| 7,268,213 B2 | 9/2007 | Dong |
| 7,329,721 B2 | 2/2008 | Kozlowski |
| 2004/0048248 A1 | 3/2004 | Prayaga |
| 2005/0272625 A1 | 12/2005 | Labib |
| 2007/0167370 A1* | 7/2007 | Gault et al. ............ 514/12 |
| 2008/0182795 A1 | 7/2008 | Wolfe |

FOREIGN PATENT DOCUMENTS

| WO | WO 03/105760 | 12/2003 |
| WO | WO 2004/103390 | 12/2004 |
| WO | WO 2008/021560 | 2/2008 |

OTHER PUBLICATIONS

Salhanick et al., Bioorganic & Medicinal Chemistry Letters, 2005, 15, 4114-4117.*
Gault, V. A. et al., "C-terminal mini-PEGylation of glucose-independent insulinotropic polypeptide exhibits metabolic stability and improved glucose homeostasis in dietary-induced diabetes", Biochemical Pharmacology, 2008, 75:2325-2333.
Green, B. D. et al., "Structurally modified analogues of glucagons-like peptide-1 (GLP-1) and glucose-dependent insulinotropic polypeptide (GIP) as future antidiabetic agents", Curr. Pharma. Design, 2004, 10:3651-3662.

* cited by examiner

*Primary Examiner* — Marcela M Cordero Garcia
*Assistant Examiner* — Kaipeen Yang
(74) *Attorney, Agent, or Firm* — Pamela C. Ball

(57) ABSTRACT

There is provided a novel series of analogues of glucose-dependent insulinotropic polypeptide compounds, pharmaceutical compositions containing said compounds, and the use of said compounds as GIP-receptor agonists or antagonists for treatment of GIP-receptor mediated conditions, such as non-insulin dependent diabetes mellitus and obesity.

16 Claims, No Drawings

ANALOGUES OF GLUCOSE-DEPENDENT INSULINOTROPIC POLYPEPTIDE

This application is a United States national stage filing under 35 U.S.C. §371 of international (PCT) application no. PCT/US2009/004543, filed Aug. 7, 2009, and designating the US, which claims priority to U.S. provisional application Nos. 61/188,192, filed Aug. 7, 2008, and 61/200,628, filed Dec. 2, 2008.

FIELD OF THE INVENTION

The present invention relates to the area of novel analogues of glucose-dependent insulinotropic polypeptide compounds, pharmaceutical compositions containing said compounds, and the use of said compounds as GIP-receptor agonists or antagonists for treatment of GIP-receptor mediated conditions, such as non-insulin dependent diabetes mellitus and obesity.

BACKGROUND ART

Glucose-dependent insulinotropic polypeptide ("GIP", also known as "gastric inhibitory polypeptide") is a 42-residue peptide secreted by enteroendorine K-cells of the small intestine into the bloodstream in response to oral nutrient ingestion. GIP inhibits the secretion of gastric acid, and it has been shown to be a potent stimulant for the secretion of insulin from pancreatic beta cells after oral glucose ingestion (the "incretin effect") (Creutzfeldt, W., et al., 1979, *Diabetologia*, 16:75-85).

Insulin release induced by the ingestion of glucose and other nutrients is due to both hormonal and neural factors (Creutzfeldt, W., et al., 1985, *Diabetologia*, 28:565-573). Several gastrointestinal regulatory peptides have been proposed as incretins, and among these candidates, only GIP and glucagon-like peptide 1 ("GLP-1") appear to fulfill the requirements to be considered physiological stimulants of postprandial insulin release (Nauck, et al., 1989, *J. Clin. Endorinol. Metab.*, 69:654-662). It has been shown that the combined effects of GIP and GLP-1 are sufficient to explain the full incretin effect of the enteroinsular axis (Fehmann, H. C., et al., 1989, *FEBS Lett.*, 252:109-112).

As is well known to those skilled in the art, the known and potential uses of GIP are varied and multitudinous. Thus, the administration of the compounds of this invention for purposes of eliciting an agonist effect can have the same effects and uses as GIP itself. These varied uses of GIP may be summarized as follows: treating a disease selected from the group consisting of type 1 diabetes, type 2 diabetes (Visboll, T., 2004, *Dan. Med. Bull.*, 51:364-70), insulin resistance (WO 2005/082928), obesity (Green, B. D., et al., 2004, *Current Pharmaceutical Design*, 10:3651-3662), metabolic disorder (Gault, V. A., et al., 2003, *Biochem. Biophys. Res. Commun.*, 308:207-213), central nervous system disease, neurodegenerative disease, congestive heart failure, hypoglycemia, and disorders wherein the reduction of food intake and weight loss are desired. In pancreatic islets, GIP not only enhances insulin secretion acutely, but it also stimulates insulin production through enhancement of proinsulin transcription and translation (Wang, et al., 1996, *Mol. Cell. Endocrinol.*, 116: 81-87) and enhances the growth and survival of pancreatic beta cells (Trumper, et al., 2003, *Diabetes*, 52:741-750). In addition to effects on the pancreas to enhance insulin secretion, GIP also has effects on insulin target tissues directly to lower plasma glucose: enhancement of glucose uptake in adipose (Eckel, et al., 1979, *Diabetes*, 28:1141-1142) and muscle (O'Harte, et al., 1998, *J. Endocrinol.*, 156:237-243), and inhibition of hepatic glucose production (Elahi, D., et al., 1986, *Can. J. Physiol. Pharmacol.*, 65:A18).

In addition, a GIP receptor antagonist in accordance with the present invention inhibits, blocks or reduces glucose absorption from the intestine of an animal. In accordance with this observation, therapeutic compositions containing GIP antagonists may be used in patients with non-insulin dependent diabetes mellitus to improve tolerance to oral glucose in mammals, such as humans, to prevent, inhibit or reduce obesity by inhibiting, blocking or reducing glucose absorption from the intestine of the mammal.

The use of unmodified GIP as a therapeutic, however, is limited by the short in vivo half-life of about 2 minutes (Said and Mutt, 1970, *Science*, 169:1217-1218). In serum, both incretins, GIP and GLP-1, are degraded by dipeptidyl peptidase IV ("DPPIV"). Improving the stability of GIP to proteolysis not only maintains the activity of GIP at its receptor but, more importantly, prevents the production of GIP fragments, some of which act as GIP receptor antagonists (Gault, et al., 2002, *J. Endocrinol.*, 175:525-533). Reported modifications have included protection of the N-terminus of GIP from proteolysis by DPPIV through modification of the N-terminal tyrosine (O'Harte, et al., 2002, *Diabetologia*, 45:1281-1291), mutation of the alanine at position 2 (Hinke, et al., 2002, *Diabetes*, 51:656-661), mutation of glutamic acid at position 3 (Gault, et al., 2003, *Biochem. Biophys. Res. Commun.*, 308:207-213), and mutation of alanine at position 13 (Gault, et al., 2003, *Cell Biol. International*, 27:41-46), The following patent applications have been filed related to the effects of GIP analogues on the function of various target organs and their potential use as therapeutic agents:

PCT publication WO 00/58360 discloses peptidyl analogues of GIP which stimulate the release of insulin. In particular, this application discloses specific peptidyl analogues comprising at least 15 amino acid residues from the N-terminal end of GIP(1-42), e.g., an analogue of GIP containing exactly one amino acid substitution or modification at positions 1, 2 and 3, such as [Pro$^3$]GIP(1-42).

PCT publication WO 98/24464 discloses an antagonist of GIP consisting essentially of a 24-amino acid polypeptide corresponding to positions 7-30 of the sequence of GIP, a method of treating non-insulin dependent diabetes mellitus and a method of improving glucose tolerance in a non-insulin dependent diabetes mellitus patient.

PCT publication WO 03/082898 discloses C-terminal truncated fragments and N-terminal modified analogues of GIP, as well as various GIP analogues with a reduced peptide bond or alterations of the amino acids close to the DPPIV-specific cleavage site. This application further discloses analogues with different linkers between potential receptor binding sites of GIP. The compounds of this application are alleged to be useful in treating GIP-receptor mediated conditions, such as non-insulin dependent diabetes mellitus and obesity.

There exists a need for improved analogues of GIP, which are stable in formulation and have long plasma half-life in vivo resulting from decreased susceptibility to proteolysis and decreased clearance while maintaining binding affinity to a GIP receptor to elicit respective agonistic or antagonistic effects. Moreover, among other therapeutic effects of the compounds of the present invention as illustrated herein, tighter control of plasma glucose levels may prevent long-term diabetic complications, thereby providing an improved quality of life for patients.

SUMMARY OF THE INVENTION

In one aspect, the invention relates to peptide variants of GIP of the following formula (I):

$$(R^2R^3)-A^1-A^2-A^3-A^4-A^5-A^6-A^7-A^8-A^9-A^{10}-A^{11}-A^{12}-A^{13}-A^{14}-A^{15}-A^{16}-A^{17}-A^{18}-A^{19}-A^{20}-A^{21}-A^{22}-A^{23}-A^{24}-A^{25}-A^{26}-A^{27}-A^{28}-A^{29}-A^{30}-A^{31}-A^{32}-A^{33}-A^{34}-A^{35}-A^{36}-A^{37}-A^{38}-A^{39}-A^{40}-A^{41}-A^{42}-A^{43}-R^1, \qquad (I)$$

wherein:

$A^1$ is deleted;

$A^2$ is Ala, Abu, D-Abu, Acc, Aib, β-Ala, D-ala, Gaba, Gly, 4Hppa, Ser, D-Ser, Thr, D-Thr, Val, D-Val, or deleted;

$A^3$ is Glu, Aib, Asp, NMe-Asp, Dhp, Dmt, NMe-Glu, 3Hyp, 4Hyp, 4Ktp, Pro, hPro, Thz, Tic, or deleted;

$A^4$ is Gly, Acc, Aib, β-Ala, or deleted;

$A^5$ is Thr, Acc, Aib, Ser, or deleted;

$A^6$ is Phe, Acc, Aib, Aic, Cha, 1Nal, 2Nal, 2-Pal, 3-Pal, 4-Pal, $(X^4,X^5,X^6,X^7,X^8)$Phe, Trp, or deleted;

$A^7$ is Ile, Abu, Acc, Aib, Ala, Cha, Leu, Nle, Phe, Tle, Val, or deleted;

$A^8$ is Ser, Aib, Chc-Ser, Thr, or deleted;

$A^9$ is Asp, Aib, Glu, or deleted;

$A^{10}$ is Tyr, Acc, Cha, 1Nal, 2Nal, 2-Pal, 3-Pal, 4-Pal, Phe, $(X^4,X^5,X^6,X^7,X^8)$Phe, or deleted;

$A^{11}$ is Ser, Acc, Aib, Thr, or deleted;

$A^{12}$ is Ile, Abu, Acc, Aib, Ala, Cha, Leu, Nle, Phe, Tle, Val, or deleted;

$A^{13}$ is Ala, β-Ala, D-Ala, Acc, Aib, Gly, Ser, or deleted;

$A^{14}$ is Met, Abu, Acc, Aib, Ala, Cha, Ile, Leu, Nle, Phe, Tle, or Val;

$A^{15}$ is Asp, Aib, or Glu;

$A^{16}$ is Lys, Amp, Apc, Arg, hArg, Orn, HN—CH(($CH_2$)$_n$—N($R^4R^5$))—C(O), Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—NH—($CH_2$)$_y$—$CH_3$), Cys(succinimide-N—($CH_2$)$_s$—NH—C(O)—($CH_2$)$_t$—$CH_3$), hCys(succinimide-N—($CH_2$)$_s$—NH—C(O)—($CH_2$)$_t$—$CH_3$), or Pen(succinimide-N—($CH_2$)$_s$—NH—C(O)—($CH_2$)$_t$—$CH_3$);

$A^{17}$ is Ile, Abu, Acc, Aib, Ala, Cha, Leu, Nle, Phe, Tle, or Val;

$A^{18}$ is His, Amp, Arg, 2-Pal, 3-Pal, 4-Pal, Phe, or Tyr;

$A^{19}$ is Gln, Aib, or Asn;

$A^{21}$ is Gln, Aib, or Asn;

$A^{21}$ is Asp, Aib, or Glu;

$A^{22}$ is Phe, Acc, Aib, Aic, Cha, 1Nal, 2Nal, 2-Pal, 3-Pal, 4-Pal, $(X^4,X^5,X^6,X^7,X^8)$Phe or Trp;

$A^{23}$ is Val, Abu, Acc, Aib, Ala, Cha, Ile, Leu, Nle, or Tle;

$A^{24}$ is Asn, Aib, or Gln;

$A^{25}$ is Trp, Acc, Aib, 1Nal, 2Nal, 2-Pal, 3-Pal, 4-Pal, Phe, or $(X^4,X^5,X^6,X^7,X^8)$Phe;

$A^{26}$ is Leu, Acc, Aib, Cha, Ile, Nle, Phe, $(X^4,X^5,X^6,X^7,X^8)$Phe, or Tle;

$A^{27}$ is Leu, Acc, Aib, Cha, Ile, Nle, Phe, $(X^4,X^5,X^6,X^7,X^8)$Phe or Tle;

$A^{28}$ is Ala, Acc, or Aib;

$A^{29}$ is Gln, Aib, Asn, or deleted;

$A^{30}$ is Lys, Amp, Apc, Arg, hArg, Orn, HN—CH(($CH_2$)$_n$—N($R^4R^5$))—C(O), Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—NH—($CH_2$)$_y$—$CH_3$), Cys(succinimide-N—($CH_2$)$_s$—NH—C(O)—($CH_2$)$_t$—$CH_3$), hCys(succinimide-N—($CH_2$)$_s$—NH—C(O)—($CH_2$)$_t$—$CH_3$), Pen(succinimide-N—($CH_2$)$_s$—NH—C(O)—($CH_2$)$_t$—$CH_3$), or deleted;

$A^{31}$ is Gly, Aib, Acc, β-Ala, 2Nal, D-2Nal, HN—CH(($CH_2$)$_n$—N($R^4R^5$))—C(O), Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—$NH_4CH_2$)$_y$—$CH_3$), Cys(succinimide-N—($CH_2$)$_s$—NH—C(O)—($CH_2$)$_t$—$CH_3$), hCys(succinimide-N—($CH_2$)$_s$—NH—C(O)—($CH_2$)$_t$—$CH_3$), Pen(succinimide-N—($CH_2$)$_s$—NH—C(O)—($CH_2$)$_t$—$CH_3$), or deleted;

$A^{32}$ is Lys, Amp, Apc, Arg, hArg, Orn, HN—CH(($CH_2$)$_n$—N($R^4R^5$))—C(O), Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—NH—($CH_2$)$_y$—$CH_3$), Cys(succinimide-N—($CH_2$)$_s$—NH—C(O)—($CH_2$)$_t$—$CH_3$), hCys(succinimide-N—($CH_2$)$_s$—NH—C(O)—($CH_2$)$_t$—$CH_3$), Pen(succinimide-N—($CH_2$)$_s$—NH—C(O)—($CH_2$)$_t$—$CH_3$), or deleted;

$A^{33}$ is Lys, Amp, Apc, Arg, hArg, Orn, Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—NH—($CH_2$)$_y$—$CH_3$), Cys(succinimide-N—($CH_2$)$_s$—NH—C(O)—($CH_2$)$_t$—$CH_3$), hCys(succinimide-N—($CH_2$)$_s$—NH—C(O)—($CH_2$)$_t$—$CH_3$), Pen(succinimide-N—($CH_2$)$_s$—NH—C(O)—($CH_2$)$_t$—$CH_3$), or deleted;

$A^{34}$ is Asn, Aib, Gln, Ser, HN—CH(($CH_2$)$_n$—N($R^4R^5$))—C(O), Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—NH—($CH_2$)$_y$—$CH_3$), Cys(succinimide-N—($CH_2$)$_s$—NH—C(O)—($CH_2$)$_t$—$CH_3$), hCys(succinimide-N—($CH_2$)$_s$—NH—C(O)—($CH_2$)$_t$—$CH_3$), Pen(succinimide-N—($CH_2$)$_s$—NH—C(O)—($CH_2$)$_t$—$CH_3$), or deleted;

$A^{35}$ is Asp, Aib, Glu, HN—CH(($CH_2$)$_n$—N($R^4R^5$))—C(O), Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—NH—($CH_2$)$_y$—$CH_3$), Cys(succinimide-N—($CH_2$)$_s$—NH—C(O)—($CH_2$)$_t$—$CH_3$), hCys(succinimide-N—($CH_2$)$_s$—NH—C(O)—($CH_2$)$_t$—$CH_3$), Pen(succinimide-N—($CH_2$)$_s$—NH—C(O)—($CH_2$)$_t$—$CH_3$), or deleted;

$A^{36}$ is Trp, Acc, Aib, 1Nal, 2Nal, 2-Pal, 3-Pal, 4-Pal, Phe, $(X^4,X^5,X^6,X^7,X^8)$Phe, HN—CH(($CH_2$)$_n$—N($R^4R^5$))—C(O), Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—NH—($CH_2$)$_y$—$CH_3$), Cys(succinimide-N—($CH_2$)$_s$—NH—C(O)—($CH_2$)$_t$—$CH_3$), hCys(succinimide-N—($CH_2$)$_s$—NH—C(O)—($CH_2$)$_t$—$CH_3$), Pen(succinimide-N—($CH_2$)$_s$—NH—C(O)—($CH_2$)$_t$—$CH_3$), or deleted;

$A^{37}$ is Lys, Amp, Apc, Arg, hArg, Orn, HN—CH(($CH_2$)$_n$—N($R^4R^5$))—C(O), Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—NH—($CH_2$)$_y$—$CH_3$), Cys(succinimide-N—($CH_2$)$_s$—NH—C(O)—

(CH$_2$)$_t$—CH$_3$), hCys(succinimide-N—(CH$_2$)$_x$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{38}$ is His, Amp, Phe, 2-Pal, 3-Pal, 4-Pal, Tyr, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{39}$ is Asn, Aib, Gln, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{40}$ is Ile, Acc, Aib, Ser, Thr, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{41}$ is Thr, Acc, Aib, Asn, Gln, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{42}$ is Gln, Aib, Acc, Asn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{43}$ is Acc, Aib, Ala, Asp, Gln, Phe, Thr, Trp, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

R$^1$ is OH, NH$_2$, (C$_1$-C$_{30}$)alkoxy, or NH—X$^2$—CH$_2$—Z$^0$, wherein X$^2$ is a (C$_1$-C$_{30}$)hydrocarbon moiety, and Z$^0$ is H, OH, CO$_2$H or CONH$_2$;

each of R$^2$, R$^3$, R$^4$ and R$^5$ is independently selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_1$-C$_{30}$)acyl, substituted (C$_2$-C$_{30}$)alkenyl, substituted (C$_2$-C$_{30}$)alkynyl, substituted aryl(C$_1$-C$_{30}$)alkyl, and substituted aryl(C$_1$-C$_{30}$)acyl; provided that when R$^2$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then R$^3$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)alkyl; further provided that when R$^4$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then R$^5$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)alkyl;

n is, independently for each occurrence, an integer from 1 to 5 inclusive;

s, t, x and y each is, independently for each occurrence, an integer from 1 to 30 inclusive;

X$^4$, X$^5$, X$^6$, X$^7$ and X$^8$ each is, independently for each occurrence, H, F, Cl, Br, I, (C$_{1-10}$)alkyl, substituted (C$_{1-10}$)alkyl, aryl, substituted aryl, OH, NH$_2$, NO$_2$, or CN; and provided that when A$^2$ is 4Hppa, then R$^2$ and R$^3$ are deleted.

A subset (A) of the compounds covered by the above formula (I) are those in which:

A$^2$ is Ala, 4Hppa, or deleted;
A$^3$ is Glu, 4Hyp, Pro, or deleted;
A$^4$ is Gly or deleted;
A$^5$ is Thr or deleted;
A$^6$ is Phe or deleted;
A$^7$ is Ile, A5c, A6c, or deleted;
A$^8$ is Ser, Chc-Ser, or deleted;
A$^9$ is Asp or deleted;
A$^{10}$ is Tyr or deleted;
A$^{11}$ is Ser, A5c, A6c, Aib, or deleted;
A$^{12}$ is Ile or deleted;
A$^{13}$ is Ala, Aib, or deleted;
A$^{14}$ is Met, A6c, or Nle;
A$^{15}$ is Asp;
A$^{16}$ is Lys;
A$^{17}$ is Ile;
A$^{18}$ is His;
A$^{19}$ is Gln;
A$^{20}$ is Gln;
A$^{21}$ is Asp;
A$^{22}$ is Phe;
A$^{23}$ is Val;
A$^{24}$ is Asn;
A$^{25}$ is Trp;
A$^{26}$ is Leu;
A$^{27}$ is Leu;
A$^{28}$ is Ala;
A$^{29}$ is Gln;
A$^{30}$ is Lys;
A$^{31}$ is Gly, Cys(Hsu), Cys(Psu), 2Nal, D-2Nal, Orn(N—C(O)—(CH$_2$)$_4$—CH$_3$), Orn(N—C(O)—(CH$_2$)$_8$—CH$_3$), Orn(N—C(O)—(CH$_2$)$_{12}$—CH$_3$), or deleted;
A$^{32}$ is Lys, Cys(Psu), or deleted;
A$^{33}$ is Lys, Cys(Psu), or deleted;
A$^{34}$ is Asn, Cys(Psu), Orn(N—C(O)—(CH$_2$)$_8$—CH$_3$), or deleted;

$A^{35}$ is Asp, Cys(Psu), or deleted;
$A^{36}$ is Trp, Cys(Psu), or deleted;
$A^{37}$ is Lys, Cys(Psu), or deleted;
$A^{38}$ is His, Cys(Psu), or deleted;
$A^{39}$ is Asn, Cys(Psu), or deleted;
$A^{40}$ is Ile, Cys(Psu), or deleted;
$A^{41}$ is Thr or deleted;
$A^{42}$ is Gln or deleted;
$A^{43}$ is Gln or deleted; and
provided that at least one of $A^2, A^3, A^4, A^5, A^6, A^7, A^8, A^9, A^{11}, A^{13}, A^{14}, A^{31}, A^{32}, A^{33}, A^{34}, A^{35}, A^{36}, A^{37}, A^{38}, A^{39}$ and $A^{40}$ is not the amino acid residue of the corresponding position of the native GIP.

A subset of the compounds of the preceding subset (A) are those in which:
$A^2$ is deleted;
$A^3$ is deleted;
$A^4$ is deleted;
$A^5$ is deleted;
$A^6$ is deleted;
$A^7$ is A5c or A6c;
$A^8$ is Ser;
$A^9$ is Asp;
$A^{10}$ is Tyr;
$A^{11}$ is Ser;
$A^{12}$ is He;
$A^{13}$ is Ala;
$A^{14}$ is Met;
$A^{31}$ is Gly, Cys(Hsu), Cys(Psu), 2Nal, D-2Nal, Orn(N—C(O)—(CH$_2$)$_4$—CH$_3$), Orn(N—C(O)—(CH$_2$)$_8$—CH$_3$), or Orn(N—C(O)—(CH$_2$)$_{12}$—CH$_3$);
$A^{32}$ is Lys or Cys(Psu);
$A^{33}$ is Lys or Cys(Psu);
$A^{34}$ is Asn, Cys(Psu), or Orn(N—C(O)—(CH$_2$)$_8$—CH$_3$);
$A^{35}$ is Asp or Cys(Psu);
$A^{36}$ is Trp or Cys(Psu);
$A^{37}$ is Lys or Cys(Psu);
$A^{38}$ is His or Cys(Psu);
$A^{39}$ is Asn or Cys(Psu);
$A^{40}$ is Ile or Cys(Psu);
$A^{41}$ is Thr;
$A^{42}$ is Gln; and
$A^{43}$ is deleted.

A subset of the compounds of the preceding subset (A) are those in which $A^{43}$ is deleted, $A^2$ is 4Hppa, and at least one of $A^3, A^7, A^{11}, A^{13}$ and $A^{14}$ is not the amino acid residue of the corresponding position of the native GIP.

Another subset of the compounds of the preceding subset (A) are those in which $A^2$ to $A^5$ and $A^{31}$ to $A^{43}$ are deleted, and at least one of $A^6, A^7, A^{11}$ and $A^{14}$ is not the amino acid residue of the corresponding position of the native GIP.

Another subset of the compounds of the preceding subset (A) are those in which $A^2$ to $A^7$ and $A^{43}$ are deleted, and at least one of $A^8$ and $A^{31}$ is not the amino acid residue of the corresponding position of the native GIP.

Another subset of the compounds of the preceding subset (A) are those in which $A^2$ to $A^5$ and $A^{43}$ are deleted, and at least one of $A^6, A^7$ and $A^{31}$ is not the amino acid residue of the corresponding position of the native GIP.

Another subset of the compounds of the preceding subset (A) are those in which $A^2$ to $A^5$ and $A^{32}$ to $A^{43}$ are deleted, and at least one of $A^6, A^7$ and $A^{31}$ is not the amino acid residue of the corresponding position of the native GIP.

Preferred compounds of formula (I) are:

Example 1:
(SEQ ID NO: 4)
(Ac-A6c$^7$)hGIP(7-42)-OH;

Example 2:
(SEQ ID NO: 5)
[Ac-A6c$^7$, Cys(Psu)$^{40}$]hGIP(7-42)-OH;

Example 3:
(SEQ ID NO: 6)
[Ac-A6c$^7$, Cys(Psu)$^{39}$]hGIP(7-42)-OH;

Example 4:
(SEQ ID NO: 7)
[Ac-A6c$^7$, Cys(Psu)$^{38}$]hGIP(7-42)-OH;

Example 5:
(SEQ ID NO: 8)
[Ac-A6c$^7$, Cys(Psu)$^{36}$]hGIP(7-42)-OH;

Example 6:
(SEQ ID NO: 9)
[Ac-A6c$^7$, Cys(Psu)$^{35}$]hGIP(7-42)-OH;

Example 7:
(SEQ ID NO: 10)
[Ac-A6c$^7$, Cys(Psu)$^{34}$]hGIP(7-42)-OH;

Example 8:
(SEQ ID NO: 11)
[Ac-A6c$^7$, Cys(Psu)$^{33}$]hGIP(7-42)-OH;

Example 9:
(SEQ ID NO: 12)
[Ac-A6c$^7$, Cys(Psu)$^{32}$]hGIP(7-42)-OH;

Example 10:
(SEQ ID NO: 13)
[Ac-A6c$^7$, Cys(Psu)$^{31}$]hGIP(7-42)-OH;

Example 11:
(SEQ ID NO: 14)
[Ac-A6c$^7$, Cys(Psu)$^{37}$]hGIP(7-42)-OH;

Example 12:
(SEQ ID NO: 15)
[Ac-A6c$^7$, Orn$^{31}$(N-C(O)-(CH$_2$)$_{12}$-CH$_3$)]hGIP(7-42)-OH;

Example 13:
(SEQ ID NO: 16)
[Ac-A6c$^7$, Orn$^{31}$(N-C(O)-(CH$_2$)$_8$-CH$_3$)]hGIP(7-42)-OH;

Example 14:
(SEQ ID NO: 17)
[A6c$^7$, Orn$^{31}$(N-C(O)-(CH$_2$)$_8$-CH$_3$)]hGIP(7-42)-OH;

Example 15:
(SEQ ID NO: 18)
[CH$_3$-(CH$_2$)$_8$-C(O)-A6c$^7$, Orn$^{31}$(N-C(O)-(CH$_2$)$_8$-CH$_3$)]hGIP(7-42)-OH;

Example 16:
(SEQ ID NO: 19)
[Ac-A6c$^7$, Orn$^{31}$(N-C(O)-(CH$_2$)$_4$-CH$_3$)]hGIP(7-42)-OH;

Example 17:
(SEQ ID NO: 20)
[A6c$^7$, Orn$^{31}$(N-C(O)-(CH$_2$)$_4$-CH$_3$)]hGIP(7-42)-OH;

Example 18:
(SEQ ID NO: 21)
[CH$_3$-(CH$_2$)$_4$-C(O)-A6c$^7$, Orn$^{31}$(N-C(O)-(CH$_2$)$_4$-CH$_3$)]hGIP(7-42)-OH;

Example 19:
(SEQ ID NO: 22)
[Ac-A6c$^7$, Orn$^{34}$(N-C(O)-(CH$_2$)$_8$-CH$_3$)]hGIP(7-42)-OH;

Example 20:
(SEQ ID NO: 23)
[A6c$^7$, Orn$^{34}$(N-C(O)-(CH$_2$)$_8$-CH$_3$)]hGIP(7-42)-OH;

Example 21:
(SEQ ID NO: 24)
[CH$_3$-(CH$_2$)$_8$-C(O)-A6c$^7$,
Orn$^{34}$(N-C(O)-(CH$_2$)$_8$-CH$_3$)]hGIP(7-42)-OH;

Example 22:
(SEQ ID NO: 25)
[Ac-A6c$^7$, Cys(Hsu)$^{31}$]hGIP(7-42)-OH;

Example 23:
(SEQ ID NO: 26)
[A6c$^7$, Cys(Hsu)$^{31}$]hGIP(7-42)-OH;

Example 24:
(SEQ ID NO: 27)
(Ac-A6c$^7$, 2Nal$^{31}$)hGIP(7-42)-OH;

Example 25:
(Ac-A6c$^7$, D-2Nal$^{31}$)hGIP(7-42)-OH;

Example 26:
(SEQ ID NO: 28)
(Ac-4Hyp$^3$, A6c$^7$)hGIP(3-42)-OH;

Example 27:
(SEQ ID NO: 29)
(Ac-A6c$^7$, Gln$^{43}$)hGIP(7-43)-OH;

Example 28:
(SEQ ID NO: 30)
(Ac-A6c$^7$, Cys(Psu)$^{31}$)hGIP(7-34)-NH$_2$;

Example 29:
(SEQ ID NO: 31)
[Ac-A6c$^7$, Cys(Psu)$^{31}$]hGIP(7-31)-NH$_2$;

Example 30:
(SEQ ID NO: 32)
[Ac-Phe$^6$, A6c$^7$, Cys(Psu)$^{31}$]hGIP(6-42)-OH;

Example 31:
(SEQ ID NO: 33)
[A6c$^7$, Cys(Psu)$^{31}$]hGIP(6-42)-OH;

Example 32:
(SEQ ID NO: 34)
(Ac-Phe$^6$, A6c$^7$)hGIP(6-30)-NH$_2$;

Example 33:
(SEQ ID NO: 35)
[Ac-Phe$^6$, A6c$^7$, Cys(Psu)$^{31}$]hGIP(6-31)-NH$_2$;

Example 34:
(SEQ ID NO: 36)
[A6c$^7$, Cys(Psu)$^{31}$]hGIP(6-31)-NH$_2$;

Example 35:
(SEQ ID NO: 37)
(A5c$^7$, Nle$^{14}$)hGIP(6-30)-NH$_2$;

Example 36:
(SEQ ID NO: 38)
(A6c$^7$, Nle$^{14}$)hGIP(6-30)-NH$_2$;

Example 37:
(SEQ ID NO: 39)
(Aib$^{11}$, Nle$^{14}$)hGIP(6-30)-NH$_2$;

Example 38:
(SEQ ID NO: 40)
[Ac-Asp$^9$, Cys(Psu)$^{33}$]hGIP(9-42)-OH;

Example 39:
(SEQ ID NO: 41)
[Orn$^{31}$(N-C(O)-(CH$_2$)$_8$-CH$_3$)]hGIP(8-42)-OH;

Example 40:
(SEQ ID NO: 42)
[Chc-Ser$^8$, Cys(Psu)$^{31}$]hGIP(8-42)-OH;

Example 41:
(SEQ ID NO: 43)
[CH$_3$-(CH$_2$)$_4$-C(O)-Ser$^8$, Cys(Psu)$^{31}$]hGIP(8-42)-OH;

Example 42:
(SEQ ID NO: 44)
(4Hppa$^2$, 4Hyp$^3$, A6c$^7$)hGIP(2-42)-OH;

Example 43:
(SEQ ID NO: 45)
(4Hppa$^2$, Pro$^3$, Nle$^{14}$)hGIP(2-42)-OH;

Example 44:
(SEQ ID NO: 46)
(4Hppa$^2$, Aib$^{13}$)hGIP(2-42)-OH);

Example 45:
(SEQ ID NO: 47)
(4Hppa$^2$, A6c$^{14}$)hGIP(2-42)-OH;

Example 46:
(SEQ ID NO: 48)
(4Hppa$^2$, A6c$^{11}$)hGIP(2-42)-OH;

and

Example 47:
(SEQ ID NO: 49)
[Aib$^2$, A5c$^{11}$, Nle$^{14}$,
Lys$^{43}$(N-C(O)-(CH$_2$)$_{10}$-CH$_3$)]hGIP(2-43)-OH.

According to another aspect of the present invention, a compound according to the present invention as summarized hereinabove and claimed in the appended claims may further comprise a covalently linked PEG moiety, in which said PEG moiety is covalently linked to the compound via a Cys(maleimide), hCys(maleimide), or Pen(maleimide) linker, to form Cys(succinimide-N-PEG), hCys(succinimide-N-PEG), or Pen(succinimide-N-PEG), wherein "succinimide-N-PEG" is either linear or branched as defined hereinbelow. Such PEG moiety has average molecular weight of from about 2,000 to about 80,000, and preferably such PEG moiety is selected from the group consisting of 5K PEG, 10K PEG, 20K PEG, 30K PEG, 40K PEG, 50K PEG, and 60K PEG, to form Cys(succinimide-N-5K PEG), Cys(succinimide-N-10K PEG), Cys(succinimide-N-20K PEG), Cys(succinimide-N-30K PEG), Cys(succinimide-N-40K PEG), Cys(succinimide-N-50K PEG), Cys(succinimide-N-60K PEG), hCys(succinimide-N-5K PEG), hCys(succinimide-N-10K PEG), hCys(succinimide-N-20K PEG), hCys(succinimide-N-30K PEG), hCys(succinimide-N-40K PEG), hCys(succinimide-N-50K PEG), hCys(succinimide-N-60K PEG), Pen(succinimide-N-5K PEG), Pen(succinimide-N-10K PEG), Pen(succinimide-N-20K PEG), Pen(succinimide-N-30K PEG), Pen(succinimide-N-40K PEG), Pen(succinimide-N-50K PEG), or Pen(succinimide-N-60K PEG).

PEGylation occurs at any one of amino acid residue positions 16, 30, and 31-43, and preferably at any one of amino acid residue positions 32, 33 and 43, whereby Cys(succinimide-N-PEG), hCys(succinimide-N-PEG), or Pen(succinimide-N-PEG) is placed in any one of such amino acid residue positions.

Further, the above formula (I) may be expanded to provide PEGylation sites at positions $A^{44}$-$A^{47}$. The C-terminus of such PEGylated compounds of the present invention may be amidated, e.g., (Ac-A6c$^7$)hGIP(7-42)-NH$_2$ (SEQ ID NO:50), or it may remain as free acid, e.g., (Ac-A6c$^7$)hGEP(7-42)-OH (SEQ ID NO:4).

DETAILED DESCRIPTION OF THE INVENTION

The application employs the following commonly understood abbreviations:

| | |
|---|---|
| Abu: | α-aminobutyric acid |
| Acc: | 1-amino-1-cyclo($C_3$-$C_9$)alkyl carboxylic acid |
| A3c: | 1-amino-1-cyclopropanecarboxylic acid |
| A4c: | 1-amino-1-cyclobutanecarboxylic acid |
| A5c: | 1-amino-1-cyclopentanecarboxylic acid |
| A6c: | 1-amino-1-cyclohexanecarboxylic acid |
| Act: | 4-amino-4-carboxytetrahydropyran |
| Ado: | 12-aminododecanoic acid |
| Aib: | α-aminoisobutyric acid |
| Aic: | 2-aminoindan-2-carboxylic acid |
| Ala or A: | alanine |
| β-Ala: | beta-alanine |
| Amp: | 4-amino-phenylalanine; |
| Apc: | 4-amino-4-carboxypiperidine: |
| Arg or R: | arginine |
| hArg: | homoarginine |
| Asn or N: | asparagine |
| Asp or D: | aspartic acid |
| Aun: | 11-aminoundecanoic acid |
| Ava: | 5-aminovaleric acid |
| Cha: | β-cyclohexylalanine |
| Chc: | cyclohexyl carboxylic acid |
| Cys or C: | cysteine |
| D-Ala: | D-alanine |
| Dhp: | 3,4-dehydroproline |
| Dmt: | 5,5-dimethylthiazolidine-4-carboxylic acid |
| Gaba: | γ-aminobutyric acid |
| Gln or Q: | glutamine |
| Glu or E: | glutamic acid |
| Gly or G: | glycine |
| His or H: | histidine |
| 4Hppa: | 3-(4-hydroxyphenyl)propionic acid |
| Hsu: | N-hexylsuccinimide |
| 3Hyp: | 3-hydroxyproline |
| 4Hyp: | 4-hydroxyproline |
| hPro: | homoproline |
| Ile or I: | isoleucine |
| 4Ktp: | 4-ketoproline |
| Leu or L: | leucine |
| Lys or K: | lysine |
| Met or M: | methionine |
| Nle: | norleucine |
| NMe-Tyr: | N-methyl-tyrosine |
| 1Nal or 1-Nal: | β-(1-naphthyl)alanine |
| 2Nal or 2-Nal: | β-(2-naphthyl)alanine |
| Nle: | norleucine |
| Nva: | norvaline |
| Orn: | ornithine |
| 2Pal or 2-Pal: | β-(2-pyridinyl)alanine |
| 3Pal or 3-Pal: | β-(3-pyridinyl)alanine |
| 4Pal or 4-Pal: | β-(4-pyridinyl)alanine |
| Pen: | penicillamine |
| Phe or F: | phenylalanine |
| (3,4,5F)Phe: | 3,4,5-trifluorophenylalanine |
| (2,3,4,5,6)Phe: | 2,3,4,5,6-pentafluorophenylalanine |
| Pro or P: | proline |
| Psu: | N-propylsuccinimide |
| Ser or S: | serine |
| Taz: | β-(4-thiazolyl)alanine |
| 3Thi: | β-(3-thienyl)alanine |
| Thr or T: | threonine |
| Thz: | thioproline |
| Tic: | tetrahydroisoquinoline-3-carboxylic acid |
| Tle: | tert-leucine |
| Trp or W: | tryptophan |
| Tyr or Y: | tyrosine |
| Val or V: | valine |

Certain other abbreviations used herein are defined as follows:

| | |
|---|---|
| Act: | acetonitrile |
| Boc: | tert-butyloxycarbonyl |
| BSA: | bovine serum albumin |
| DCM: | dichloromethane |
| DIPEA: | diisopropylethyl amine |
| DMF: | dimethylformamide |
| DTT: | dithiothrieitol |
| ESI: | electrospray ionization |
| Fmoc: | 9-fluorenylmethyloxycarbonyl |
| HBTU: | 2-(1H-benzotriazole-1-yl)-1,1,3,3-tetramethyluronium hexafluorophosphate |
| HOBT: | 1-hydroxybenzotriazole |
| HPLC: | high performance liquid chromatography |
| IBMX: | isobutylmethylxanthine |
| LC-MS: | liquid chromatography-mass spectrometry |
| Mtt: | methyltrityl |
| NMP: | N-methylpyrrolidone |
| 5K PEG: | polyethylene glycol, which may include other functional groups or moieties such as a linker, and which is either linear or branched as defined hereinbelow, with an average total molecular weight of about 5,000 |
| 10K PEG: | polyethylene glycol, which may include other functional groups or moieties such as a linker, and which is either linear or branched as defined hereinbelow, with an average total molecular weight of about 10,000 |
| 20K PEG: | polyethylene glycol, which may include other functional groups or moieties such as a linker, and which is either linear or branched as defined hereinbelow, with an average total molecular weight of about 20,000 |
| 30K PEG: | polyethylene glycol, and which is either linear or branched as defined hereinbelow, which may include other functional groups or moieties such as a linker, with an average total molecular weight of about 30,000 |
| 40K PEG: | polyethylene glycol, which may include other functional groups or moieties such as a linker, and which is either linear or branched as defined hereinbelow, with an average total molecular weight of about 40,000 |
| 50K PEG: | polyethylene glycol, which may include other functional groups or moieties such as a linker, and which is either linear or branched as defined hereinbelow, with an average total molecular weight of about 50,000 |
| 60K PEG: | polyethylene glycol, which may include other functional groups or moieties such as a linker, and which is either linear or branched as defined hereinbelow, with an average total molecular weight of about 60,000 |
| tBu: | tert-butyl |
| TIS: | triisopropylsilane |
| Trt: | trityl |
| TFA: | trifluoro acetic acid |
| Z: | benzyloxycarbonyl |

"Cys(succinimide-N-alkyl)" has the structure of:

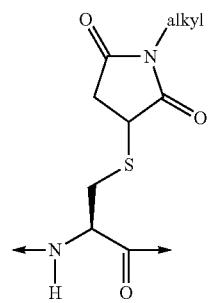

"Cys(Hsu)" has the structure of:

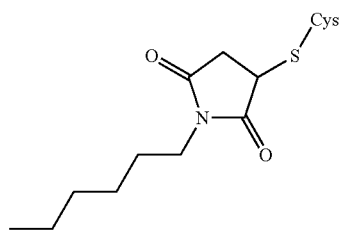

"Cys(Psu)" has the structure of:

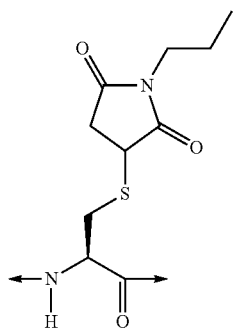

"Orn(N—C(O)—(CH₂)₁₂—CH₃)" has the structure of:

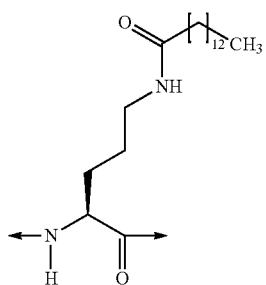

"Cys(succinimide-N—(CH₂)$_x$—C(O)—NH—(CH₂)$_y$—CH₃)" has the structure of:

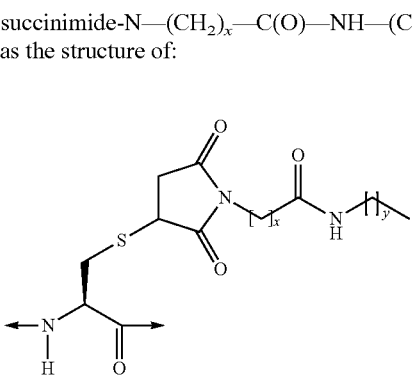

wherein, x=1-30, and y=1-30.

"hCys(succinimide-N—(CH₂)$_x$—C(O)—NH—(CH₂)$_y$—CH₃)" has the structure of:

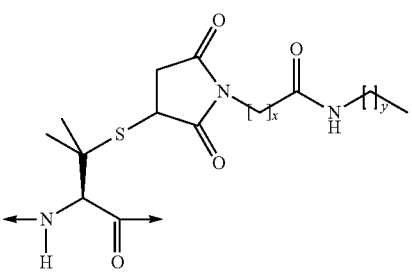

wherein, x=1-30, and y=1-30.

"Pen(succinimide-N—(CH₂)$_x$—C(O)—NH—(CH₂)$_y$—CH₃)" has the structure of:

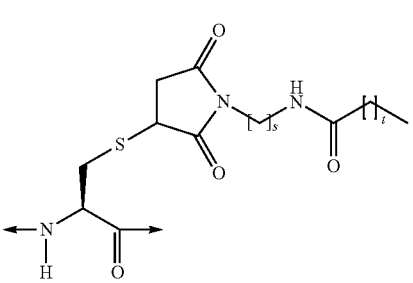

wherein, x=1-30, and y=1-30.

"Cys(succinimide-N—(CH₂)$_s$—NH—C(O)—(CH₂)$_t$—CH₃)" has the structure of:

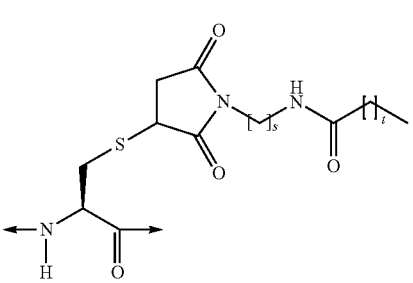

wherein, s=1-30, and t=1-30.

"hCys(succinimide-N—(CH$_2$)$_s$—NH—C(O)—(CH$_2$)$_t$—CH$_3$)" has the structure of:

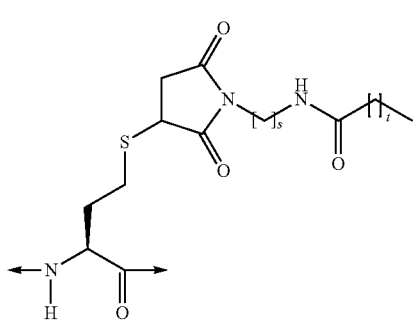

wherein s=1-30, and t=1-30.

"Pen(succinimide-N—(CH$_2$)$_s$—NH—C(O)—(CH$_2$)$_t$—CH$_3$)" has the structure of:

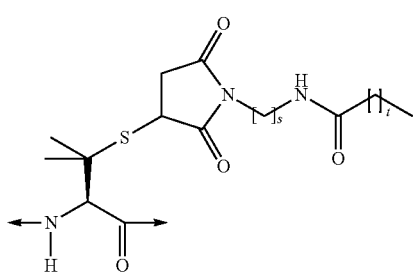

wherein s=1-30, and t=1-30.

"Cys(succinimide-N-PEG)" has the structure of:

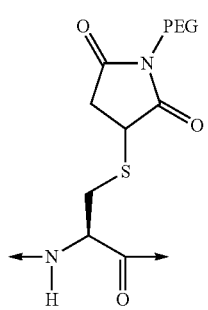

"hCys(succinimide-N-PEG)" has the structure of:

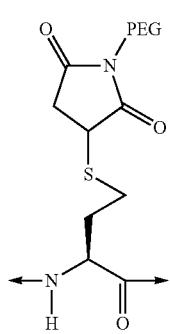

"Pen(succinimide-N-PEG)" has the structure of:

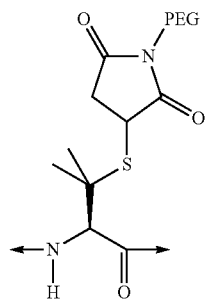

"Cys(succinimide-N—(CH$_2$)$_2$—C(O)NH—(CH$_2$)$_3$-PEG)" has the structure of:

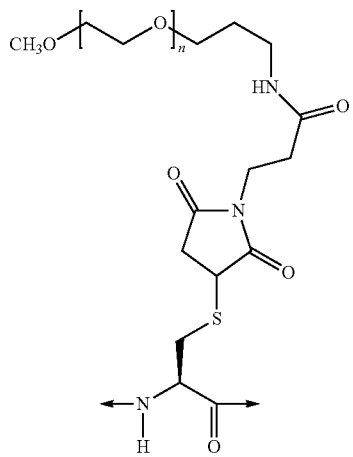

"Cys(succinimide-N—(CH$_2$)$_2$—C(O)NH—(CH$_2$)$_3$—O—CH$_2$—CH(PEG)-CH$_2$-PEG)" has the structure of:

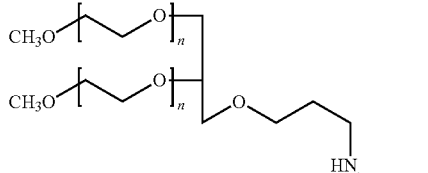
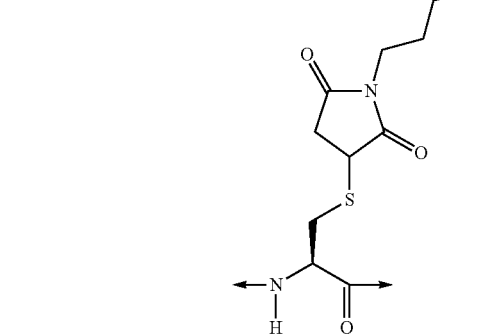

With the exception of the N-terminal amino acid, all abbreviations (e.g., Ala) of amino acids in this disclosure stand for the structure of —NH—C(R)(R')—CO—, wherein R and R' each is, independently, hydrogen or the side chain of an amino acid (e.g., R=CH$_3$ and R'=H for Ala), or R and R' may be joined to form a ring system. For the N-terminal amino acid, the abbreviation stands for the structure of (R$^2$R$^3$)N—C(R)(R')—CO—, wherein R$^2$ and R$^3$ are as defined in the above formula (I).

The term "(C$_1$-C$_{30}$)hydrocarbon moiety" encompasses alkyl, alkenyl and alkynyl, and in the case of alkenyl and alkynyl there are C$_2$-C$_{30}$.

A peptide of this invention is also denoted herein by another format, e.g., (A5c$^2$)hGIP(1-42)-OH (SEQ ID NO:3), with the substituted amino acids from the natural sequence placed between the brackets (e.g., A5c$^2$ for Ala$^2$ in hGIP). The numbers between the parentheses refer to the number of amino acids present in the peptide (e.g., hGIP(1-42)-OH (SEQ ID NO:1) is amino acids 1 through 42 of the peptide sequence for hGIP). The designation "NH$_2$" in hGIP(1-30)-NH$_2$ (SEQ ID NO:2) indicates that the C-terminus of the peptide is amidated; hGIP(1-42) (SEQ ID NO:1) or hGIP(1-42)-OH (SEQ ID NO:1) means that the C-terminus is the free acid.

Human GIP ("hGIP") has the amino acid sequence of:

```
                                           (SEQ ID NO: 1)
Tyr-Ala-Glu-Gly-Thr-Phe-Ile-Ser-Asp-Tyr-Ser-
1               5                   10

Ile-Ala-Met-Asp-Lys-Ile-His-Gln-Gln-Asp-Phe-
            15                  20

Val-Asn-Trp-Leu-Leu-Ala-Gln-Lys-Gly-Lys-Lys-
        25                  30

Asn-Asp-Trp-Lys-His-Asn-Ile-Thr-Gln.
    35                  40
```

"Acyl" refers to R"-C(O)—, where R" is H, alkyl, substituted alkyl, heteroalkyl, substituted heteroalkyl, alkenyl, substituted alkenyl, aryl, alkylaryl, or substituted alkylaryl.

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —C$_{1-20}$ alkyl substituted with halogens, —CF$_3$, —OCH$_3$, —OCF$_3$, and —(CH$_2$)$_{0-20}$—COOH. In different embodiments 1, 2, 3 or 4 substituents are present. The presence of —(CH$_2$)$_{0-20}$—COOH results in the production of an alkyl acid. Examples of alkyl acids containing, or consisting of, —(CH$_2$)$_{0-20}$—COOH include 2-norbornane acetic acid, tert-butyric acid and 3-cyclopentyl propionic acid.

"Heteroalkyl" refers to an alkyl wherein one of more of the carbon atoms in the hydrocarbon group are replaced with one or more of the following groups: amino, amido, —O—, —S— or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen, —OH, —CN, —SH, —NH$_2$, —NHCH$_3$, —NO$_2$, —C$_{1-20}$ alkyl substituted with halogens, —CF$_3$, —OCH$_3$, —OCF$_3$, and —(CH$_2$)$_{0-20}$—COOH. In different embodiments 1, 2, 3 or 4 substituents are present.

"Alkenyl" refers to a hydrocarbon group made up of two or more carbons wherein one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen, —OH, —CN, —SH, —NH$_2$, —NHCH$_3$, —NO$_2$, —C$_{1-20}$ alkyl substituted with halogens, —CF$_3$, —OCH$_3$, —OCF$_3$, and —(CH$_2$)$_{0-20}$—COOH. In different embodiments 1, 2, 3 or 4 substituents are present.

"Aryl" refers to an optionally substituted aromatic group with at least one ring having a conjugated pi-electron system, containing up to three conjugated or fused ring systems. Aryl includes carbocyclic aryl, heterocyclic aryl and biaryl groups. Preferably, the aryl is a 5 or 6 membered ring. Preferred atoms for a heterocyclic aryl are one or more sulfur, oxygen, and/or nitrogen. Examples of aryl include phenyl, 1-naphthyl, 2-naphthyl, indole, quinoline, 2-imidazole, and 9-anthracene. Aryl substituents are selected from the group consisting of —C$_{1-20}$ alkyl, —C$_{1-20}$ alkoxy, halogen, —OH, —CN, —SH, —NH$_2$, —NO$_2$, —C$_{1-20}$ alkyl substituted with halogens, —CF$_3$, —OCF$_3$, and —(CH$_2$)$_{0-20}$—COOH. In different embodiments the aryl contains 0, 1, 2, 3, or 4 substituents.

"Alkylaryl" refers to an "alkyl" joined to an "aryl".

Synthesis

The peptides of this invention can be prepared by standard solid phase peptide synthesis. See, e.g., Stewart, J. M., et al., 1984, *Solid Phase Synthesis*, Pierce Chemical Co., 2d ed. If R$^1$ is NH—X$^2$—CH$_2$—CONH$_2$, i.e., Z$^0$=CONH$_2$, the synthesis of the peptide starts with Fmoc-HN—X$^2$—CH$_2$—CONH$_2$ which is coupled to Rink amide MBHA resin. If R$^1$ is NH—X$^2$—CH$_2$—COOH, i.e., Z$^0$=COOH, the synthesis of the peptide starts with Fmoc-HN—X$^2$—CH$_2$—COOH which is coupled to Wang resin. For this particular step, 2 molar equivalents of Fmoc-HN—X$^2$—COOH, HBTU and HOBt and 10 molar equivalents of DIPEA are used. The coupling time is about 8 hours.

In the synthesis of a GIP analogue of this invention containing A5c, A6c, and/or Aib, the coupling time is 2 hrs for these residues and the residue immediately following them.

The substituents R$^2$ and R$^3$ of the above generic formula can be attached to the free amine of the N-terminal amino acid A$^1$ by standard methods known in the art. For example, alkyl groups, e.g., (C$_1$-C$_{30}$)alkyl, can be attached using reductive alkylation. Hydroxyalkyl groups, e.g., (C$_1$-C$_{30}$)hydroxyalkyl, can also be attached using reductive alkylation wherein the free hydroxy group is protected with a tert-butyl ester. Acyl groups, e.g., —C(O)X$^3$, can be attached by coupling the free acid, e.g., —X$^3$COOH, to the free amine of the N-terminal amino acid by mixing the completed resin with 3 molar equivalents of both the free acid and diisopropylcarbodiimide in methylene chloride for about one hour. If the free acid contains a free hydroxy group, e.g., 3-fluoro-4-hydroxyphenylacetic acid, then the coupling should be performed with an additional 3 molar equivalents of HOBT.

The following examples describe synthetic methods for making a peptide of this invention, which methods are well-known to those skilled in the art. Other methods are also known to those skilled in the art. The examples are provided for the purpose of illustration and are not meant to limit the scope of the present invention in any manner.

EXAMPLE 2

[Ac-A6c⁷, Cys(Psu)⁴⁰]hGIP(7-42)-OH

Solid-phase peptide synthesis was used to assemble the peptide using microwave-assisted Fmoc Chemistry on a Liberty Peptide Synthesizer (CEM; Matthews, N.C., USA) at the 0.1 mmole scale. Pre-loaded Fmoc-Gln(Trt)-Wang resin (0.59 mmole/g; Novabiochem, San Diego, Calif., USA) was used to generate the C-terminal acid peptide. The resin (0.17 g) was placed in a 50 ml conical tube along with 15 ml of dimethylformamide (DMF) and loaded onto a resin position on the synthesizer. The resin was then quantitatively transferred to the reaction vessel via the automated process. The standard Liberty synthesis protocol for 0.1 mmole scale synthesis was used. This protocol involves deprotecting the N-terminal Fmoc moiety via an initial treatment with 7 ml of 20% piperidine, containing 0.1M N-hydroxybenzotriazole (HOBT), in DMF. The initial deprotection step was for 30 seconds with microwave power (45 watts, maximum temperature of 75° C.), and nitrogen bubbling (3 seconds on/7 seconds off). The reaction vessel was then drained and a second piperidine treatment, identical to the first treatment, except that it was for a 3-minute duration. The resin was then drained and thoroughly washed with DMF several times. The protected amino acid, Fmoc-Thr(tBu)-OH, prepared as 0.2M stock solution in DMF, was then added (2.5 ml, 5 equivalents), followed by 1.0 ml of 0.45M (4.5 eq.) HBTU [2-(1H-benzo-triazole-1-yl)-1,1,3,3-tetramethyluronium hexafluorophosphate] in DMF. This was followed by the addition of 0.5 ml of 2M (10 eq.) DIPEA (diisopropylethylamine) in NMP (N-methylpyrrollidinone). The coupling step was performed for 5 minutes using 20 watts of microwave power, a max temperature of 75° C., and the same rate of nitrogen bubbling.

Following the initial coupling step, the reaction vessel was drained to waste and the coupling step repeated. Cycle 2 was then initiated similar to cycle 1. All amino acids were introduced similarly and a double-coupling strategy was employed throughout the entire sequence. Cycles 1-3, 19-20, 25-26, and 30-34 contained a capping procedure immediately following the coupling step. Capping was performed by adding 7 ml of 0.5M acetic anhydride, containing 0.015M HOBT in NMP, along with 2 ml of the 2M DIPEA solution using a multi-step microwave protocol: 50 watts of power for 30 seconds (65° C. max temperature), followed by 30 seconds of microwave power off, followed by a second round of 30 seconds of microwave power on (50 watts), and then again 30 seconds of no microwave power. The resin was then drained and thoroughly washed with DMF. The following amino acids (Advanced Chemtech; Louisville, Ky., USA) were used: Cycle 1: Fmoc-Thr(OtBu)-OH; Cycle 2: Fmoc-Cys(Trt)-OH; Cycle 3: Fmoc-Asn(Trt)-OH; Cycle 4: Fmoc-His(Trt)-OH; Cycle 5: Fmoc-Lys(Boc)-OH; Cycle 6: Fmoc-Trp(Boc)-OH; Cycle 7: Fmoc-Asp(OtBu)-OH; Cycle 8: Fmoc-Asn(Trt)-OH; Cycle 9: Fmoc-Lys(Boc)-OH; Cycle 10: Fmoc-Lys(Boc)-OH; Cycle 11: Fmoc-Gly-OH; Cycle 12: Fmoc-Lys(Boc)-OH; Cycle 13: Fmoc-Gln(Trt)-OH; Cycle 14: Fmoc-Ala-OH; Cycle 15: Fmoc-Leu-OH; Cycle 16: Fmoc-Leu-OH; Cycle 17: Fmoc-Trp(Boc)-OH; Cycle 18: Fmoc-Asn(Trt)-OH; Cycle 19: Fmoc-Val-OH; Cycle 20: Fmoc-Phe-OH; Cycle 21: Fmoc-Asp(OtBu)-OH; Cycle 22: Fmoc-Gln(Trt)-OH; Cycle 23: Fmoc-Gln(Trt)-OH; Cycle 24: Fmoc-His(Trt)-OH; Cycle 25: Fmoc-Ile-OH; Cycle 26: Fmoc-Lys(Boc)-OH; Cycle 27: Fmoc-Asp(OtBu)-OH; Cycle 28: Fmoc-Met-OH; Cycle 29: Fmoc-Ala-OH; Cycle 30: Fmoc-Ile-OH; Cycle 31: Fmoc-Tyr(tBu)-Ser(psiMe,Me, Pro)-OH; Cycle 32: Fmoc-Asp(OtBu)-OH; Cycle 33: Fmoc-Ser(tBu)-OH; and Cycle 34: Fmoc-A6c-OH. Once the peptide backbone was complete, the resin was treated with piperidine solution to remove the N-terminal Fmoc group, followed by treatment with the standard capping procedure in order to acetylate the N-terminus. The resin was then thoroughly washed with DMF and then transferred back to the 50 ml conical tube using DMF as the transfer solvent.

The resin was deprotected and cleaved from the resin via treatment with 5 ml of the following reagent; 5% TIS, 2% water, 5% (w/v) dithiothrieitol (DTT), 88% TFA, and allowed to mix for 3.5 hours. The filtrate was collected into 45 ml of cold anhydrous ethyl ether. The precipitate was pelleted for 10 minutes at 3500 RPM in a refrigerated centrifuge. The ether was decanted, and the peptide re-suspended in fresh ether. The ether workup was performed a total of 2 times. Following the last ether wash the peptide was allowed to air dry to remove residual ether. The peptide pellet was resuspended in 8 ml of acetonitrile (Acn) followed by 8 ml of de-ionized water, and allowed to fully dissolve. The peptide solution was then analyzed by mass spectrometry. Mass analysis employing electrospray ionization identified a main product containing a mass of 4358.0 Daltons; corresponding to the acetylated, linear product. The crude product (approximately 500 mg) was analysed by HPLC, employing a 250× 4.6 mm C18 column (Phenomenex; Torrance, Calif., USA) using a gradient of 2-80% acetonitrile (0.1% TFA) over 30 minutes. Analytical HPLC identified a product with 38% purity. The crude peptide was then purified on a preparative HPLC equipped with a C18 reverse phase column using a 10-60% acetonitrile (0.1% TFA) over 50 minutes at a 10 ml/min flowrate. The purified peptide was then lyophilized yielding 15 mg of peptide. The linear peptide was then derivatized with N-propylmaleimide (Pma) to generate the propylsuccinimide (Psu) derivative on the Cysteine side chain. The purified linear peptide was brought up in water, adjusted to pH 6.5 with ammonium carbonate, at 5 mg/ml. Five equivalents of Pma was added with constant stirring for 30 seconds. The derivatized peptide solution was then analyzed by mass spectrometry. Mass analysis identified a main product containing a mass of 4498.6 Daltons; corresponding to the desired Psu derivatized product. The product was then re-purified via preparative HPLC using a similar gradient as before. The purified product was analyzed by HPLC for purity (95.2%) and mass spectrometry (4498.6 Daltons) and subsequently lyophilized. Following lyophillization, 4.3 mg of purified product was obtained representing a 1% yield.

EXAMPLE 12

[Ac-Ac6c⁷, Orn(N—C(O)—(CH$_2$)$_{12}$—CH$_3$)³¹]hGIP(7-42)-OH

Solid-phase peptide synthesis was used to assemble the peptide using microwave-assisted Fmoc Chemistry on a Liberty Peptide Synthesizer (CEM; Matthews, N.C., USA) at the 0.1 mmole scale. Pre-loaded Fmoc-Gln(Trt)-Wang resin (0.59 mmole/g; Novabiochem, San Diego, Calif., USA) was used to generate the C-terminal acid peptide. The resin (0.17 g) was placed in a 50 ml conical tube along with 15 ml of dimethylformamide (DMF) and loaded onto a resin position on the synthesizer. The resin was then quantitatively transferred to the reaction vessel via the automated process. The standard Liberty synthesis protocol for 0.1 mmole scale synthesis was used. This protocol involves deprotecting the N-terminal Fmoc moiety via an initial treatment with 7 ml of 20% piperidine, containing 0.1M N-hydroxybenzotriazole (HOBT), in DMF. The initial deprotection step was for 30 seconds with microwave power (45 watts, maximum temperature of 75° C.), and nitrogen bubbling (3 seconds on/7 seconds off). The reaction vessel was then drained and a second piperidine treatment, identical to the first treatment, except that it was for a 3-minute duration. The resin was then drained and thoroughly washed with DMF several times. The protected amino acid, Fmoc-Thr(tBu)-OH, prepared as 0.2M stock solution in DMF, was then added (2.5 ml, 5 eq.), followed by 1.0 ml of 0.45M (4.5 eq.) HBTU [2-(1H-benzotriazole-1-yl)-1,1,3,3-tetramethyluronium hexafluorophosaphate] in DMF. This was followed by the addition of 0.5 ml of 2M (10 eq.) DIPEA (diisopropylethylamine) in NMP (N-methylpyrrollidinone). The coupling step was performed for 5 minutes using 20 watts of microwave power, a max temperature of 75° C., and the same rate of nitrogen bubbling.

Following the initial coupling step the reaction vessel was drained to waste and the coupling step repeated. Cycle 2 was then initiated similar to cycle 1. All amino acids were introduced similarly and a double-coupling strategy was employed throughout the entire sequence. Cycles 1-3, 19-20, 25-26, and 30-34 contained a capping procedure immediately following the coupling step. Capping was performed by adding 7 ml of 0.5M acetic anhydride, containing 0.015M HOBT in NMP, along with 2 ml of the 2M DIPEA solution using a multi-step microwave protocol: 50 watts of power for 30 seconds (65° C. max temperature), followed by 30 seconds of microwave power off, followed by a second round of 30 seconds of microwave power on (50 watts), and then again 30 seconds of no microwave power. The resin was then drained and thoroughly washed with DMF. The following amino acids (Advanced Chemtech; Louisville, Ky., USA) were used; Cycle 1: Fmoc-Thr(tBu)-OH; Cycle 2: Fmoc-Ile-OH; Cycle 3: Fmoc-Asn(Trt)-OH; Cycle 4: Fmoc-His(Trt)-OH; Cycle 5: Fmoc-Lys(Boc)-OH; Cycle 6: Fmoc-Trp(Boc)-OH; Cycle 7: Fmoc-Asp(OtBu)-OH; Cycle 8: Fmoc-Asn(Trt)-OH; Cycle 9: Fmoc-Lys(Boc)-OH; Cycle 10: Fmoc-Lys(Boc)-OH; Cycle 11: Fmoc-Orn(Mtt)-OH; Cycle 12: Fmoc-Lys(Boc)-OH; Cycle 13: Fmoc-Gln(Trt)-OH; Cycle 14: Fmoc-Ala-OH; Cycle 15: Fmoc-Leu-OH; Cycle 16: Fmoc-Leu-OH; Cycle 17: Fmoc-Trp(Boc)-OH; Cycle 18: Fmoc-Asn(Trt)-OH; Cycle 19: Fmoc-Val-OH; Cycle 20: Fmoc-Phe-OH; Cycle 21: Fmoc-Asp(OtBu)-OH; Cycle 22: Fmoc-Gln(Trt)-OH; Cycle 23: Fmoc-Gln(Trt)-OH; Cycle 24: Fmoc-His(Trt)-OH; Cycle 25: Fmoc-Ile-OH; Cycle 26: Fmoc-Lys(Boc)-OH; Cycle 27: Fmoc-Asp(OtBu)-OH; Cycle 28: Fmoc-Met-OH; Cycle 29: Fmoc-Ala-OH; Cycle 30: Fmoc-Ile-OH; Cycle 31: Fmoc-Tyr(tBu)-Ser(psiMe,Me,Pro)-OH; Cycle 32: Fmoc-Asp(OtBu)-OH; Cycle 33: Fmoc-Ser(tBu)-OH; and Cycle 34: Fmoc-A6c-OH. The coupling protocol for Fmoc-His(Trt)-OH was a slightly modified version of the standard protocol. The microwave power was off for the first 2 minutes, followed by 4 minutes with microwave power on (20 watts; max temperature of 50° C.). Once the peptide backbone was complete, the resin was treated with piperidine solution to remove the N-terminal Fmoc group, followed by treatment with the standard capping procedure in order to acetylate the N-terminus. The resin was then treated with 12 ml of 1% trifluoroacetic acid (TFA)/5% triisopropylsilane (TIS) in dichloromethane (DCM) for 5 minutes and a $N_2$ sparge rate of 5 seconds on and 10 seconds off. The resin was then drained and again treated with the 1% TFA/5% TIS in DCM solution for 5 minutes. This was performed a total of 7 times to effectively remove the Mtt moiety from the Ornithine side chain. The resin was thoroughly washed with DCM several times, and then treated with the standard piperidine treatment in order to neutralize residual TFA salt on the δN of ornithine. Myristic acid, 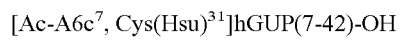 $(CH_3—(CH_2)_{12}—COOH$; Aldrich, St. Louis, Mo., USA) prepared as a 0.2M solution in DMF, was coupled to the ornithine side chain using the standard amino acid coupling protocol. The resin was then thoroughly washed with DMF and then transferred back to the 50 ml conical tube using DMF as the transfer solvent.

The resin was deprotected and cleaved from the resin via treatment with 5 ml of the following reagent; 5% TIS, 2% water, 5% (w/v) dithiothrieitol (DTT), 88% TFA, and allowed to mix for 3.5 hours. The filtrate was collected into 45 ml of cold anhydrous ethyl ether. The precipitate was pelleted for 10 minutes at 3500 RPM in a refrigerated centrifuge. The ether was decanted, and the peptide re-suspended in fresh ether. The ether workup was performed a total of 2 times. Following the last ether wash the peptide was allowed to air dry to remove residual ether. The peptide pellet was resuspended in 8 ml of acetonitrile (Acn) followed by 8 ml of de-ionized water, and allowed to fully dissolve. The peptide solution was then analyzed by mass spectrometry. Mass analysis employing electrospray ionization identified a main product containing a mass of 4636.5 Daltons; corresponding to the desired product. The crude product was analysed by HPLC, employing a 250×4.6 mm C18 column (Phenomenex; Torrance, Calif., USA) using a gradient of 2-80% acetonitrile (0.1% TFA) over 30 minutes. Analytical HPLC identified a product with 37% purity. The peptide was then purified on a preparative HPLC equipped with a C18 column using a similar elution gradient. The purified product was re-analyzed by HPLC for purity (95.20%) and mass spectrometry (4636.6 Daltons) and subsequently lyophilized. Following lyophillization, 3 mg of purified product was obtained representing a 0.6% yield.

EXAMPLE 22

[Ac-A6c$^7$, Cys(Hsu)$^{31}$]hGUP(7-42)-OH

Solid-phase peptide synthesis was used to assemble the peptide using microwave-assisted Fmoc Chemistry on a Liberty Peptide Synthesizer (CEM; Matthews, N.C., USA) at the 0.1 mmole scale. Pre-loaded Fmoc-Gln(Trt)-Wang resin (0.59 mmole/g; Novabiochem, San Diego, Calif., USA) was used to generate the C-terminal acid peptide. The resin (0.17 g) was placed in a 50 ml conical tube along with 15 ml of dimethylformamide (DMF) and loaded onto a resin position on the synthesizer. The resin was then quantitatively transferred to the reaction vessel via the automated process. The standard Liberty synthesis protocol for 0.1 mmole scale synthesis was used. This protocol involves deprotecting the N-terminal Fmoc moiety via an initial treatment with 7 ml of 20% piperidine, containing 0.1M N-hydroxybenzotriazole (HOBT), in DMF. The initial deprotection step was for 30 seconds with microwave power (45 watts, maximum temperature of 75° C.), and nitrogen bubbling (3 seconds on/7 seconds off). The reaction vessel was then drained and a second piperidine treatment, identical to the first treatment, except that it was for a 3-minute duration. The resin was then drained and thoroughly washed with DMF several times. The protected amino acid, Fmoc-Thr(tBu)-OH, prepared as 0.2M stock solution in DMF, was then added (2.5 ml, 5 eq.), followed by 1.0 ml of 0.45M (4.5 eq.) HBTU [2-(1H-benzotriazole-1-yl)-1,1,3,3-tetramethyluronium hexafluorophosphate] in DMF. This was followed by the addition of 0.5 ml of 2M (10 eq.) DIPEA (diisopropylethylamine) in NMP (N-methylpyrrollidinone). The coupling step was performed for 5 minutes using 20 watts of microwave power, a max temperature of 75° C., and the same rate of nitrogen bubbling.

Following the initial coupling step the reaction vessel was drained to waste and the coupling step repeated. Cycle 2 was then initiated similar to cycle 1. All amino acids were introduced similarly and a double-coupling strategy was employed throughout the entire sequence. Cycles 1-3, 19-20, 25-26, and 30-34 contained a capping procedure immediately following the coupling step. Capping was performed by adding 7 ml of 0.5M acetic anhydride, containing 0.015M HOBT in NMP, along with 2 ml of the 2M DIPEA solution using a multi-step microwave protocol: 50 watts of power for 30 seconds (65° C. max temperature), followed by 30 seconds of microwave power off, followed by a second round of 30 seconds of microwave power on (50 watts), and then again 30 seconds of no microwave power. The resin was then drained and thoroughly washed with DMF. The following amino acids (Advanced Chemtech, Louisville, Ky., USA) were used: Cycle 1: Fmoc-Thr(OtBu)-OH; Cycle 2: Fmoc-Ile-OH; Cycle 3: Fmoc-Asn(Trt)-OH; Cycle 4: Fmoc-His(Trt)-OH; Cycle 5: Fmoc-Lys(Boc)-OH; Cycle 6: Fmoc-Trp(Boc)-OH; Cycle 7: Fmoc-Asp(OtBu)-OH; Cycle 8: Fmoc-Asn(Trt)-OH; Cycle 9: Fmoc-Lys(Boc)-OH; Cycle 10: Fmoc-Lys(Boc)-OH; Cycle 11: Fmoc-Cys(Trt)-OH; Cycle 12: Fmoc-Lys(Boc)-OH; Cycle 13: Fmoc-Gln(Trt)-OH; Cycle 14: Fmoc-Ala-OH; Cycle 15: Fmoc-Leu-OH; Cycle 16: Fmoc-Leu-OH; Cycle 17: Fmoc-Trp(Boc)-OH; Cycle 18: Fmoc-Asn(Trt)-OH; Cycle 19: Fmoc-Val-OH; Cycle 20: Fmoc-Phe-OH; Cycle 21: Fmoc-Asp(OtBu)-OH; Cycle 22: Fmoc-Gln(Trt)-OH; Cycle 23: Fmoc-Gln(Trt)-OH; Cycle 24: Fmoc-His(Trt)-OH; Cycle 25: Fmoc-Ile-OH; Cycle 26: Fmoc-Lys(Boc)-OH; Cycle 27: Fmoc-Asp(OtBu)-OH; Cycle 28: Fmoc-Met-OH; Cycle 29: Fmoc-Ala-OH; Cycle 30: Fmoc-Ile-OH; Cycle 31: Fmoc-Tyr(tBu)-Ser(psiMe,Me,Pro)-OH; Cycle 32: Fmoc-Asp(OtBu)-OH; Cycle 33: Fmoc-Ser(tBu)-OH; and Cycle 34: Fmoc-A6c-OH. Once the peptide backbone was complete, the resin was treated with piperidine solution to remove the N-terminal Fmoc group, followed by treatment with the standard capping procedure in order to acetylate the N-terminus. The resin was then thoroughly washed with DMF and then transferred back to the 50 ml conical tube using DMF as the transfer solvent.

The resin was deprotected and cleaved from the resin via treatment with 5 ml of the following reagent; 5% TIS, 2% water, 5% (w/v) dithiothrieitol (DTT), 88% TFA, and allowed to mix for 3.5 hours. The filtrate was collected into 45 ml of cold anhydrous ethyl ether. The precipitate was pelleted for 10 minutes at 3500 RPM in a refrigerated centrifuge. The ether was decanted, and the peptide re-suspended in fresh ether. The ether workup was performed a total of 2 times. Following the last ether wash the peptide was allowed to air dry to remove residual ether. The peptide pellet was resuspended in 8 ml of acetonitrile (Acn) followed by 8 ml of de-ionized water, and allowed to fully dissolve. The peptide solution was then analyzed by mass spectrometry. Mass analysis employing electrospray ionization identified a main product containing a mass of 4414.9 Daltons; corresponding to the linear product. The crude product (approximately 500 mg) was analysed by HPLC, employing a 250×4.6 mm C18 column (Phenomenex; Torrance, Calif., USA) using a gradient of 2-80% acetonitrile (0.1% TFA) over 30 minutes. Analytical HPLC identified a product with 58% purity. The crude peptide was then derivatized with N-hexylmaleimide (Hma) to generate the hexylsuccinimide (Hsu) derivative on the Cysteine side chain. The crude linear peptide was brought up in water, adjusted to pH 6.5 with ammonium carbonate, at 5 mg/ml. Five equivalents of Hma was added with constant stirring for 30 seconds. Excess Hma was quenched using 5 eq. of dithiothreitol (DTT). The derivatized peptide solution was then analyzed by mass spectrometry. Mass analysis identified a main product containing a mass of 4596.1 Daltons; corresponding to the desired Hsu derivatized product. The product was then re-purified via preparative HPLC using a similar gradient as before. The purified product was analyzed by HPLC for purity (95.4%) and mass spectrometry (4596.4 Daltons) and subsequently lyophilized. Following lyophillization, 28.1 mg of purified product was obtained representing a 6.1% yield.

The PEGylated GIP compounds disclosed herein can be synthesized substantially according to the procedure described for the synthesis of the compound of Example 2, by using PEG-maleimide as the starting material instead of N-propylmaleimide used in Example 2.

Other peptides of the invention can be prepared by a person of ordinary skill in the art using synthetic procedures analogous to those disclosed in the foregoing examples. Physical data for the compounds exemplified herein are given in Table 1.

TABLE 1

| Example Number | Mol. Wt. (Expected) | Mol. Wt. (ESI-MS) | % Purity (HPLC) |
|---|---|---|---|
| 1 | 4368.92 | 4368.8 | 96.70 |
| 2 | 4498.06 | 4498.6 | 95.20 |
| 3 | 4497.12 | 4497.5 | 99.90 |
| 4 | 4474.08 | 4473.9 | 99.90 |
| 5 | 4425.01 | 4425.0 | 99.90 |
| 6 | 4496.13 | 4496.5 | 99.90 |
| 7 | 4497.12 | 4496.7 | 99.90 |
| 8 | 4483.05 | 4482.4 | 99.90 |
| 9 | 4483.05 | 4482.7 | 99.90 |
| 10 | 4554.17 | 4554.0 | 99.90 |
| 11 | 4483.05 | 4482.7 | 98.40 |
| 12 | 4636.38 | 4636.6 | 95.20 |
| 13 | 4580.27 | 4580.7 | 96.70 |
| 14 | 4538.23 | 4538.8 | 99.90 |
| 15 | 4692.48 | 4693.1 | 95.00 |
| 16 | 4524.16 | 4524.9 | 96.20 |
| 17 | 4482.13 | 4482.6 | 99.90 |
| 18 | 4580.27 | 4580.9 | 95.70 |
| 19 | 4523.22 | 4523.7 | 95.50 |
| 20 | 4481.18 | 4481.4 | 99.90 |
| 21 | 4635.43 | 4636.0 | 95.30 |
| 22 | 4596.25 | 4596.4 | 95.40 |
| 23 | 4554.21 | 4554.6 | 95.80 |
| 24 | 4509.11 | 4509.8 | 99.10 |
| 25 | 4509.11 | 4509.9 | 99.90 |
| 26 | 4787.37 | 4788.4 | 99.90 |
| 27 | 4497.05 | 4496.8 | 99.90 |
| 28 | 3530.07 | 3530.0 | 99.90 |
| 29 | 3159.62 | 3159.6 | 96.40 |
| 30 | 4701.35 | 4701.7 | 96.40 |
| 31 | 4659.31 | 4660.0 | 95.10 |
| 32 | 3064.50 | 3064.7 | 99.90 |
| 33 | 3306.80 | 3306.7 | 96.30 |
| 34 | 3264.76 | 3264.6 | 98.20 |
| 35 | 2990.40 | 2990.8 | 96.83 |
| 36 | 3004.42 | 3004.7 | 99.90 |
| 37 | 2990.44 | 2990.8 | 97.20 |
| 38 | 4270.80 | 4270.6 | 99.90 |
| 39 | 4413.06 | 4413.5 | 99.90 |
| 40 | 4497.12 | 4497.6 | 96.90 |
| 41 | 4485.11 | 4485.7 | 96.40 |
| 42 | 4893.49 | 4894.4 | 99.90 |
| 43 | 4847.45 | 4848.1 | 99.90 |
| 44 | 4911.51 | 4911.4 | 99.90 |
| 45 | 4891.45 | 4891.0 | 99.90 |
| 46 | 4935.58 | 4935.8 | 99.90 |
| 47 | 5150.9 | 5151.4 | 99.9 |

Functional Assays

A. In Vitro hGIP Receptor Binding Assay

Membranes for in vitro receptor binding assays were prepared by homogenizing the CHO-K1 clonal cells expressing the human recombinant GIP receptor, with a Brinkman Polytron (setting 6, 15 sec), in ice-cold 50 mM Tris-HCl and then subjected to two centrifugations at 39,000 g for 10 minutes, with a resuspension in fresh buffer in between. For the assay, aliquots of the washed membrane preparations were incubated (100 minutes at 25° C. with 0.05 nM [$^{125}$I]GIP (approximately 2200 Ci/mmol) in 50 mM Tris-HCl, 0.1 mg/ml bacitracin, and 0.1% BSA. The final assay volume was 0.5 ml. The incubations were terminated by rapid filtration through GF/C filters (pre-soaked in 0.5% polyethylenimine) using a Brandel filtration manifold. Each tube and filter were then washed three times with 5-ml aliquots of ice-cold buffer. Specific binding was defined as the total radioligand bound minus that bound in the presence of 1000 nM GIP. In vitro hGIP receptor binding data for the compounds exemplified herein are given in Table 2.

B. Human and Rat Plasma Half-Life Assay

GIP peptide (50 μL 1 mg/ml) was added to 450 μL plasma (human or rat), vertexed briefly and incubated at 37° C. 50 μl, was removed at various times, like at 0, 1, 2, 3, 4, 8, 24, 32, 48, 56, 72 hours, mixed with 5 μL formic acid and 150 μL acetonitrile in a microcentrifuge tube, vertexed, and centrifuged for 10 minutes at 10K rpm. The supernatant was transferred to an injection vial and analyzed by LC-MS. The LC-MS system consisted of an API4000 mass spectrometer with an ESI probe. Positive ion mode and full scan detection were used. HPLC separation was carried out on a Luna 3μ C8 (2), 2×30 mm column with a gradient from 90% A to 90% B in 10 minutes at a flow rate of 0.3 ml/min. Buffer A was 1% formic acid in water and buffer B was 1% formic acid acetonitrile. Human and rat plasma half-life data for the compounds exemplified herein are given in Table 2.

TABLE 2

| Example Number | Ki (nM) | Human Plasma T½ (hr) | Rat Plasma T½ (hr) |
|---|---|---|---|
| 1 | N/A | >72 | 11.0 |
| 2 | 532.19 | 13.7 | 7.2 |
| 3 | 75.73 | 16.4 | 5.6 |
| 4 | 332.97 | 10.0 | 6.0 |
| 5 | 442.49 | 7.8 | 8.5 |
| 6 | 486.41 | 8.0 | 3.2 |
| 7 | 735.40 | 7.9 | 1.6 |
| 8 | 416.57 | N/A | N/A |
| 9 | 686.96 | N/A | N/A |
| 10 | 963.06 | 8.0 | 2.6 |
| 11 | 127.00 | N/A | N/A |
| 12 | 178.00 | 7.3 | >72 |
| 13 | N/A | 17.8 | 19.0 |
| 14 | N/A | 4.1 | 15.3 |
| 15 | N/A | 5.2 | >72 |
| 16 | N/A | >50 | 30.0 |
| 17 | N/A | >50 | 9.4 |
| 18 | N/A | 13.8 | 6.3 |
| 19 | N/A | 18.9 | 10.7 |
| 20 | 274.00 | 9.4 | 13.9 |
| 21 | 163.50 | 8.0 | >72 |
| 22 | N/A | 7.7 | 5.0 |
| 23 | 772.00 | 11.7 | 5.3 |
| 24 | 194.33 | 26.3 | 12.2 |
| 25 | 159.39 | >50 | 13.7 |
| 26 | 546.10 | 30.1 | 17.5 |
| 27 | 7.92 | N/A | N/A |
| 28 | 114.78 | 8.8 | 4.1 |
| 29 | 48.32 | 12.2 | 7.0 |
| 30 | 574.00 | 7.2 | 7.6 |
| 31 | 277.01 | 4.4 | 5.1 |
| 32 | 68.54 | 24.1 | 60.3 |
| 33 | 77.48 | 13.6 | 10.2 |
| 34 | 101.42 | 11.3 | 7.4 |
| 35 | 734.33 | 16.5 | 23.0 |
| 36 | 212.33 | 21.9 | 21.6 |
| 37 | 170.00 | 13.5 | 28.5 |

TABLE 2-continued

| Example Number | Ki (nM) | Human Plasma T½ (hr) | Rat Plasma T½ (hr) |
|---|---|---|---|
| 38 | 472.00 | N/A | N/A |
| 39 | N/A | 31.1 | 13.7 |
| 40 | 403.33 | 4.1 | 6.9 |
| 41 | 205.48 | 5.9 | 3.7 |
| 42 | 293.90 | >51 | 10.3 |
| 43 | 800.01 | >53 | 2.3 |
| 44 | 12.89 | 48.8 | 9.9 |
| 45 | 50.43 | 64.2 | 4.3 |
| 46 | 91.78 | 30.8 | 11.9 |
| 47 | N/A | N/A | N/A |

C. Determination of Cyclic AMP Stimulation

1×10⁵ CHO-K1 cells expressing the human recombinant GIP receptor or RIN-5F insulinoma cells were seeded overnight into 24-well cell culture plates (Corning Incorporate, Corning, N.Y., USA). For the assay, the cells were preincubated in 500 μl of Hanks balanced salt solution (Sigma, St. Louis, Mo., USA) with 0.55 mM IBMX (Sigma, St. Louis, Mo., USA) adjusted to pH 7.3 for 10 minutes. GIP or its analogs was then added at a concentration of 100 nM. Following a 30-minute incubation at 37° C., the plates were placed on ice and 500 μl of ice-cold absolute ethanol was added to stop the reaction. The contents of the wells were collected, spun at 2,700 g for 20 minutes at 4° C. to remove cellular debris. The cAMP levels in the supernatants were determined by radioimmunoassay (New England Nuclear, Boston, Mass., USA).

Administration

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC, eluting with TFA containing buffer solutions) can be converted into another salt, such as an acetate salt by dissolving the peptide in a small amount of 0.25 N acetic acid aqueous solution. The resulting solution is applied to a semi-prep HPLC column (Zorbax, 300 SB, C-8). The column is eluted with (1) 0.1N ammonium acetate aqueous solution for 0.5 hrs, (2) 0.25N acetic acid aqueous solution for 0.5 hrs, and (3) a linear gradient (20% to 100% of solution B over 30 minutes) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. In general, an effective dosage for the activities of this invention is in the range of $1\times10^{-7}$ to 200 mg/kg/day, preferably $1\times10^{4}$ to 100 mg/kg/day, which can be administered as a single dose or divided into multiple doses.

The compounds of this invention can be administered by oral, parenteral (e.g., intramuscular, intraperitoneal, intravenous or subcutaneous injection, or implant), nasal, vaginal, rectal, sublingual, or topical routes of administration, and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include, without limitation, pharmaceutically acceptable emulsions, solutions, suspensions, syrups, elixirs, and the like, containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include, without limitation, sterile aqueous or non-aqueous solutions, suspensions, emulsions, and the like. Examples of non-aqueous solvents or vehicles include propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221 teaches polymeric sustained release compositions comprising a bioactive agent and chitosan. U.S. Pat. No. 5,916,883 teaches sustained release compositions comprising a bioactive agent and cyclodextrin. PCT publication WO99/38536 teaches absorbable sustained release compositions of a bioactive agent. PCT publication WO00/04916 teaches a process for making microparticles comprising a therapeutic agent such as a peptide in an oil-in-water process.

Unless defined otherwise, all technical and scientific terms used herein have the same meaning as commonly understood by one of ordinary skill in the art to which this invention belongs. Also, all publications, patent applications, patents and other references mentioned herein are hereby incorporated by reference, each in its entirety.

What is claimed is:

1. A compound of formula (I), $$R^2R^3)\text{-}A^1\text{-}A^2\text{-}A^3\text{-}A^4\text{-}A^5\text{-}A^6\text{-}A^7\text{-}A^8\text{-}A^9\text{-}A^{10}\text{-}A^{11}\text{-}A^{12}\text{-}A^{13}\text{-}A^{14}\text{-}A^{15}\text{-}A^{16}\text{-}A^{17}\text{-}A^{18}\text{-}A^{19}\text{-}A^{20}\text{-}A^{21}\text{-}A^{22}\text{-}A^{23}\text{-}A^{24}\text{-}A^{25}\text{-}A^{26}\text{-}A^{27}\text{-}A^{28}\text{-}A^{29}\text{-}A^{30}\text{-}A^{31}\text{-}A^{32}\text{-}A^{33}\text{-}A^{34}\text{-}A^{35}\text{-}A^{36}\text{-}A^{37}\text{-}A^{38}\text{-}A^{39}\text{-}A^{40}\text{-}A^{41}\text{-}A^{42}\text{-}A^{43}\text{-}R^1,$$
(I)

wherein:
- $A^1$ is deleted;
- $A^2$ is Ala, Abu, D-Abu, Acc, Aib, β-Ala, D-Ala, Gaba, Gly, 4Hppa, Ser, D-Ser, Thr, D-Thr, Val, D-Val, or deleted;
- $A^3$ is Glu, Aib, Asp, NMe-Asp, Dhp, Dmt, NMe-Glu, 3Hyp, 4Hyp, 4Ktp, Pro, hPro, Thz, Tic, or deleted;
- $A^4$ is Gly, Acc, Aib, β-Ala, or deleted;
- $A^5$ is Thr, Acc, Aib, Ser, or deleted;
- $A^6$ is Phe, Acc, Aib, Aic, Cha, 1Nal, 2Nal, 2-Pal, 3-Pal, 4-Pal, $(X^4,X^5,X^6,X^7,X^8)$Phe, Trp, or deleted;
- $A^7$ is Ile, Abu, Acc, Aib, Ala, Cha, Leu, Nle, Phe, Tle, Val, or deleted;
- $A^8$ is Ser, Aib, Chc-Ser, Thr, or deleted;
- $A^9$ is Asp, Aib, Glu, or deleted;
- $A^{10}$ is Tyr, Acc, Cha, 1Nal, 2Nal, 2-Pal, 3-Pal, 4-Pal, Phe, $(X^4,X^5,X^6,X^7,X^8)$Phe, or deleted;
- $A^{11}$ is Ser, Acc, Aib, Thr, or deleted;
- $A^{12}$ is Ile, Abu, Acc, Aib, Ala, Cha, Leu, Nle, Phe, Tle, Val, or deleted;
- $A^{13}$ is Ala, p-Ala, D-Ala, Acc, Aib, Gly, Ser, or deleted;
- $A^{14}$ is Met, Abu, Acc, Aib, Ala, Cha, Ile, Leu, Nle, Phe, Tle, or Val;
- $A^{15}$ is Asp, Aib, or Glu;
- $A^{16}$ is Lys, Amp, Apc, Arg, hArg, Orn, HN—CH$((CH_2)_n$—N$(R^4R^5))$—C(O), Cys(succinimide-N-alkyl), hCys (succinimide-N-alkyl), Pen(succinimide-N-alkyl), Cys (succinimide-N—$(CH_2)_x$—C(O)—NH—$(CH_2)_y$—CH$_3$), hCys(succinimide-N—$(CH_2)_x$—C(O)—NH—$(CH_2)_y$—CH$_3$), Pen(succinimide-N—$(CH_2)_x$—C(O)—NH—$(CH_2)_y$—CH$_3$), Cys(succinimide-N—$(CH_2)_s$—NH—C(O)—$(CH_2)_t$—CH$_3$), hCys(succinimide-N—$(CH_2)_s$—NH—C(O)—$(CH_2)_t$—CH$_3$), or Pen (succinimide-N—$(CH_2)_s$—NH—C(O)—$(CH_2)_t$—CH$_3$);
- $A^{17}$ is Ile, Abu, Acc, Aib, Ala, Cha, Leu, Nle, Phe, Tle, or Val;
- $A^{18}$ is His, Amp, Arg, 2-Pal, 3-Pal, 4-Pal, Phe, or Tyr;
- $A^{19}$ is Gln, Aib, or Asn;
- $A^{20}$ is Gln, Aib, or Asn;
- $A^{21}$ is Asp, Aib, or Glu;
- $A^{22}$ is Phe, Acc, Aib, Aic, Cha, 1Nal, 2Nal, 2-Pal, 3-Pal, 4-Pal, $(X^4,X^5,X^6,X^7,X^8)$Phe or Trp;
- $A^{23}$ is Val, Abu, Acc, Aib, Ala, Cha, Ile, Leu, Nle, or Tle;
- $A^{24}$ is Asn, Aib, or Gln;
- $A^{25}$ is Trp, Acc, Aib, 1Nal, 2Nal, 2-Pal, 3-Pal, 4-Pal, Phe, or $(X^4,X^5,X^6,X^7,X^8)$Phe;
- $A^{26}$ is Leu, Acc, Aib, Cha, Ile, Nle, Phe, $(X^4,X^5,X^6,X^7,X^8)$Phe, or Tle;
- $A^{27}$ is Leu, Acc, Aib, Cha, Ile, Nle, Phe, $(X^4,X^5,X^6,X^7,X^8)$Phe or Tle;
- $A^{28}$ is Ala, Acc, or Aib;
- $A^{29}$ is Gln, Aib, Asn, or deleted;
- $A^{30}$ is Lys, Amp, Apc, Arg, hArg, Orn, HN—CH$((CH_2)_n$—N$(R^4R^5))$—C(O), Cys(succinimide-N-alkyl), hCys (succinimide-N-alkyl), Pen(succinimide-N-alkyl), Cys (succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

$A^{31}$ is Gly, Aib, Acc, β-Ala, 2Nal, D-2Nal, HN—CH$((CH_2)_n$—N$(R^4R^5))$—C(O), Cys(succinimide-N-alkyl), hCys(succinimide-N-alkyl), Pen(succinimide-N-alkyl), Cys(succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

$A^{32}$ is Lys, Amp, Apc, Arg, hArg, Orn, HN—CH$((CH_2)_n$—N$(R^4R^5))$—C(O), Cys(succinimide-N-alkyl), hCys(succinimide-N-alkyl), Pen(succinimide-N-alkyl), Cys(succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

$A^{33}$ is Lys, Amp, Apc, Arg, hArg, Orn, Cys(succinimide-N-alkyl), hCys(succinimide-N-alkyl), Pen(succinimide-N-alkyl), Cys(succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

$A^{34}$ is Asn, Aib, Gln, Ser, HN—CH$((CH_2)_n$—N$(R^4R^5))$—C(O), Cys(succinimide-N-alkyl), hCys(succinimide-N-alkyl), Pen(succinimide-N-alkyl), Cys(succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

$A^{35}$ is Asp, Aib, Glu, HN—CH$((CH_2)_n$—N$(R^4R^5))$—C(O), Cys(succinimide-N-alkyl), hCys(succinimide-N-alkyl), Pen(succinimide-N-alkyl), Cys(succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

$A^{36}$ is Trp, Acc, Aib, 1Nal, 2Nal, 2-Pal, 3-Pal, 4-Pal, Phe, $(X^4,X^5,X^6,X^7,X^8)$Phe, HN—CH$((CH_2)_n$—N$(R^4R^5))$—C(O), Cys(succinimide-N-alkyl), hCys(succinimide-N-alkyl), Pen(succinimide-N-alkyl), Cys(succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

$A^{37}$ is Lys, Amp, Apc, Arg, hArg, Orn, HN—CH$((CH_2)_n$—N$(R^4R^5))$—C(O), Cys(succinimide-N-alkyl), hCys(succinimide-N-alkyl), Pen(succinimide-N-alkyl), Cys(succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

$A^{38}$ is His, Amp, Phe, 2-Pal, 3-Pal, 4-Pal, Tyr, HN—CH$((CH_2)_n$—N$(R^4R^5))$—C(O), Cys(succinimide-N-alkyl), hCys(succinimide-N-alkyl), Pen(succinimide-N-alkyl), Cys(succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

$A^{39}$ is Asn, Aib, Gln, HN—CH$((CH_2)_n$—N$(R^4R^5))$—C(O), Cys(succinimide-N-alkyl), hCys(succinimide-N-alkyl), Pen(succinimide-N-alkyl), Cys(succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

$A^{40}$ is Ile, Acc, Aib, Ser, Thr, HN—CH$((CH_2)_n$—N$(R^4R^5))$—C(O), Cys(succinimide-N-alkyl), hCys(succinimide-N-alkyl), Pen(succinimide-N-alkyl), Cys(succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

$A^{41}$ is Thr, Acc, Aib, Asn, Gln, HN—CH$((CH_2)_n$—N$(R^4R^5))$—C(O), Cys(succinimide-N-alkyl), hCys(succinimide-N-alkyl), Pen(succinimide-N-alkyl), Cys(succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

$A^{42}$ is Gln, Aib, Acc, Asn, HN—CH$((CH_2)_n$—N$(R^4R^5))$—C(O), Cys(succinimide-N-alkyl), hCys(succinimide-N-alkyl), Pen(succinimide-N-alkyl), Cys(succinimide-N—$(CH_2)_x$—C(O)—NH—$(CH_2)_y$—$CH_3$), hCys(succinimide-N—$(CH_2)_x$—C(O)—NH—$(CH_2)_y$—$CH_3$), Pen(succinimide-N—$(CH_2)_x$—C(O)—NH—$(CH_2)_y$—$CH_3$), Cys(succinimide-N—$(CH_2)_s$—NH—C(O)—$(CH_2)_t$—$CH_3$), hCys(succinimide-N—$(CH_2)_s$—NH—C(O)—$(CH_2)_t$—$CH_3$), Pen(succinimide-N—$(CH_2)_s$—NH—C(O)—$(CH_2)_t$—$CH_3$), or deleted;

A$^{43}$ is Acc, Aib, Ala, Asp, Gln, Phe, Thr, Trp, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

R$^1$ is OH, NH$_2$, (C$_1$-C$_{30}$)alkoxy, or NH—X$^2$—CH$_2$—Z$^0$, wherein X$^2$ is a (C$_1$-C$_{30}$)hydrocarbon moiety, and Z$^0$ is H, OH, CO$_2$H or CONH$_2$;

each of R$^2$, R$^3$, R$^4$ and R$^5$ is independently selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_1$-C$_{30}$)acyl, substituted (C$_2$-C$_{30}$)alkenyl, substituted (C$_2$-C$_{30}$)alkynyl, substituted aryl(C$_1$-C$_{30}$)alkyl, and substituted aryl(C$_1$-C$_{30}$)acyl; provided that when R$^2$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then R$^3$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)alkyl; further provided that when R$^4$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then R$^5$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)alkyl;

n is, independently for each occurrence, an integer from 1 to 5 inclusive;

s, t, x and y each is, independently for each occurrence, an integer from 1 to 30 inclusive;

X$^4$, X$^5$, X$^6$, X$^7$ and X$^8$ each is, independently for each occurrence, H, F, Cl, Br, I, (C$_{1-10}$)alkyl, substituted (C$_{1-10}$)alkyl, aryl, substituted aryl, OH, NH$_2$, NO$_2$, or CN; and provided that when A$^2$ is 4Hppa, then R$^2$ and R$^3$ are deleted; and provided that at least two of A$^2$, A$^3$, A$^4$, A$^5$, A$^6$, A$^7$, A$^8$, A$^9$, A$^{11}$, A$^{13}$, A$^{14}$, A$^{31}$, A$^{32}$, A$^{33}$, A$^{34}$, A$^{35}$, A$^{36}$, A$^{37}$, A$^{38}$, A$^{39}$ and A$^{40}$ is not the amino acid residue of the corresponding position of native hGIP;

or a pharmaceutically acceptable salt thereof.

2. A compound according to claim 1, wherein:
A$^2$ is Ala, 4Hppa, or deleted;
A$^3$ is Glu, 4Hyp, Pro, or deleted;
A$^4$ is Gly or deleted;
A$^5$ is Thr or deleted;
A$^6$ is Phe or deleted;
A$^7$ is Ile, A5c, A6c, or deleted;
A$^8$ is Ser, Chc-Ser, or deleted;
A$^9$ is Asp or deleted;
A$^{10}$ is Tyr or deleted;
A$^{11}$ is Ser, A5c, A6c, Aib, or deleted;
A$^{12}$ is Ile or deleted;
A$^{13}$ is Ala, Aib, or deleted;
A$^{14}$ is Met, A6c, or Nle;
A$^{15}$ is Asp;
A$^{16}$ is Lys;
A$^{17}$ is Ile;
A$^{18}$ is His;
A$^{19}$ is Gln;
A$^{20}$ is Gln;
A$^{21}$ is Asp;
A$^{22}$ is Phe;
A$^{23}$ is Val;
A$^{24}$ is Asn;
A$^{25}$ is Trp;
A$^{26}$ is Leu;
A$^{27}$ is Leu;
A$^{28}$ is Ala;
A$^{29}$ is Gln;
A$^{30}$ is Lys;
A$^{31}$ is Gly, Cys(Hsu), Cys(Psu), 2Nal, D-2Nal, Orn(N—C(O)—(CH$_2$)$_4$—CH$_3$), Orn(N—C(O)—(CH$_2$)$_8$—CH$_3$), Orn(N—C(O)—(CH$_2$)$_{12}$—CH$_3$), or deleted;
A$^{32}$ is Lys, Cys(Psu), or deleted;
A$^{33}$ is Lys, Cys(Psu), or deleted;
A$^{34}$ is Asn, Cys(Psu), Orn(N—C(O)—(CH$_2$)$_8$—CH$_3$), or deleted;
A$^{35}$ is Asp, Cys(Psu), or deleted;
A$^{36}$ is Trp, Cys(Psu), or deleted;
A$^{37}$ is Lys, Cys(Psu), or deleted;
A$^{38}$ is His, Cys(Psu), or deleted;
A$^{39}$ is Asn, Cys(Psu), or deleted;
A$^{40}$ is Ile, Cys(Psu), or deleted;
A$^{41}$ is Thr or deleted;
A$^{42}$ is Gln or deleted; and
A$^{43}$ is Gln or deleted;
or a pharmaceutical salt thereof.

3. A compound according to claim 2, wherein said compound is:

[Ac-A6c$^7$, Cys(Psu)$^{40}$]hGIP(7-42)-OH; (SEQ ID NO: 5)

[Ac-A6c$^7$, Cys(Psu)$^{39}$]hGIP(7-42)-OH; (SEQ ID NO: 6)

[Ac-A6c$^7$, Cys(Psu)$^{38}$]hGIP(7-42)-OH; (SEQ ID NO: 7)

[Ac-A6c$^7$, Cys(Psu)$^{36}$]hGIP(7-42)-OH; (SEQ ID NO: 8)

[Ac-A6c$^7$, Cys(Psu)$^{35}$]hGIP(7-42)-OH; (SEQ ID NO: 9)

[Ac-A6c$^7$, Cys(Psu)$^{34}$]hGIP(7-42)-OH; (SEQ ID NO: 10)

[Ac-A6c$^7$, Cys(Psu)$^{33}$]hGIP(7-42)-OH; (SEQ ID NO: 11)

[Ac-A6c$^7$, Cys(Psu)$^{32}$]hGIP(7-42)-OH; (SEQ ID NO: 12)

[Ac-A6c$^7$, Cys(Psu)$^{31}$]hGIP(7-42)-OH; (SEQ ID NO: 13)

[Ac-A6c$^7$, Cys(Psu)$^{37}$]hGIP(7-42)-OH; (SEQ ID NO: 14)

[Ac-A6c$^7$, Orn$^{31}$(N-C(O)-(CH$_2$)$_{12}$-CH$_3$)]hGIP(7-42)-OH; (SEQ ID NO: 15)

[Ac-A6c$^7$, Orn$^{31}$(N-C(O)-(CH$_2$)$_8$-CH$_3$)]hGIP(7-42)-OH; (SEQ ID NO: 16)

[A6c$^7$, Orn$^{31}$(N-C(O)-(CH$_2$)$_8$-CH$_3$)]hGIP(7-42)-OH; (SEQ ID NO: 17)

```
                                                  (SEQ ID NO: 18)
[CH₃-(CH₂)₈-C(O)-A6c⁷,
Orn³¹(N-C(O)-(CH₂)₈-CH₃)]hGIP(7-42)-OH;

(SEQ ID NO: 19)
[Ac-A6c⁷, Orn³¹(N-C(O)-(CH₂)₄-CH₃)]hGIP(7-42)-OH;

(SEQ ID NO: 20)
[A6c⁷, Orn³¹(N-C(O)-(CH₂)₄-CH₃)]hGIP(7-42)-OH;

(SEQ ID NO: 21)
[CH₃-(CH₂)₄-C(O)-A6c⁷,
Orn³¹(N-C(O)-(CH₂)₄-CH₃)]hGIP(7-42)-OH;

(SEQ ID NO: 22)
[Ac-A6c⁷, Orn³⁴(N-C(O)-(CH₂)₈-CH₃)]hGIP(7-42)-OH;

(SEQ ID NO: 23)
[A6c⁷, Orn³⁴(N-C(O)-(CH₂)₈-CH₃)]hGIP(7-42)-OH;

(SEQ ID NO: 24)
[CH₃-(CH₂)₈-C(O)-A6c⁷,
Orn³⁴(N-C(O)-(CH₂)₈-CH₃)]hGIP(7-42)-OH;

(SEQ ID NO: 25)
[Ac-A6c⁷, Cys(Hsu)³¹]hGIP(7-42)-OH;

(SEQ ID NO: 26)
[A6c⁷, Cys(Hsu)³¹]hGIP(7-42)-OH;

(SEQ ID NO: 27)
(Ac-A6c⁷, 2Nal³¹)hGIP(7-42)-OH;

(Ac-A6c⁷, D-2Nal³¹)hGIP(7-42)-OH;

(SEQ ID NO: 28)
(Ac-4Hyp³, A6c⁷)hGIP(3-42)-OH;

(SEQ ID NO: 29)
(Ac-A6c⁷, Gln⁴³)hGIP(7-43)-OH;

(SEQ ID NO: 30)
(Ac-A6c⁷, Cys(Psu)³¹]hGIP(7-34)-NH₂;

(SEQ ID NO: 31)
[Ac-A6c⁷, Cys(Psu)³¹]hGIP(7-31)-NH₂;

(SEQ ID NO: 32)
[Ac-Phe⁶, A6c⁷, Cys(Psu)³¹]hGIP(6-42)-OH;

(SEQ ID NO: 33)
[A6c⁷, Cys(Psu)³¹]hGIP(6-42)-OH;

(SEQ ID NO: 34)
(Ac-Phe⁶, A6c⁷)hGIP(6-30)-NH₂;

(SEQ ID NO: 35)
[Ac-Phe⁶, A6c⁷, Cys(Psu)³¹]hGIP(6-31)-NH₂;

(SEQ ID NO: 36)
[A6c⁷, Cys(Psu)³¹]hGIP(6-31)-NH₂;

(SEQ ID NO: 37)
(A5c⁷, Nle¹⁴)hGIP(6-30)-NH₂;

(SEQ ID NO: 38)
(A6c⁷, Nle¹⁴)hGIP(6-30)-NH₂;

(SEQ ID NO: 39)
(Aib¹¹, Nle¹⁴)hGIP(6-30)-NH₂;

(SEQ ID NO: 40)
[Ac-Asp⁹, Cys(Psu)³³]hGIP(9-42)-OH;

(SEQ ID NO: 41)
[Orn³¹(N-C(O)-(CH₂)₈-CH₃)]hGIP(8-42)-OH;

(SEQ ID NO: 42)
[Chc-Ser⁸, Cys(Psu)³¹]hGIP(8-42)-OH;

(SEQ ID NO: 43)
[CH₃-(CH₂)₄-C(O)-Ser⁸, Cys(Psu)³¹]hGIP(8-42)-OH;

(SEQ ID NO: 44)
(4Hppa², 4Hyp³, A6c⁷)hGIP(2-42)-OH;

(SEQ ID NO: 45)
(4Hppa², Pro³, Nle¹⁴)hGIP(2-42)-OH;

(SEQ ID NO: 46)
(4Hppa², Aib¹³)hGIP(2-42)-OH;

(SEQ ID NO: 47)
(4Hppa², A6c¹⁴)hGIP(2-42)-OH;

(SEQ ID NO: 48)
(4Hppa², A6c¹¹)hGIP(2-42)-OH;
or
                                                  (SEQ ID NO: 49)
[Aib², A5c¹¹, Nle¹⁴,
Lys⁴³(N-C(O)-(CH₂)₁₀-CH₃)]hGIP(2-43)-OH;

or a pharmaceutically acceptable salt thereof.
```

4. A compound according to claim 2, wherein:
$A^2$ is deleted;
$A^3$ is deleted;
$A^4$ is deleted;
$A^5$ is deleted;
$A^6$ is deleted;
$A^7$ is A5c or A6c;
$A^8$ is Ser;
$A^9$ is Asp;
$A^{10}$ is Tyr;
$A^{11}$ is Ser;
$A^{12}$ is Ile;
$A^{13}$ is Ala;
$A^{14}$ is Met;
$A^{31}$ is Gly, Cys(Hsu), Cys(Psu), 2Nal, D-2Nal, Orn(N—C(O)—(CH₂)₄—CH₃), Orn(N—C(O)—(CH₂)₈—CH₃), or Orn(N—C(O)—(CH₂)₁₂—CH₃);
$A^{32}$ is Lys or Cys(Psu);
$A^{33}$ is Lys or Cys(Psu);
$A^{34}$ is Asn, Cys(Psu), or Orn(N—C(O)—(CH₂)₈—CH₃);
$A^{35}$ is Asp or Cys(Psu);
$A^{36}$ is Trp or Cys(Psu);
$A^{37}$ is Lys or Cys(Psu);
$A^{38}$ is His or Cys(Psu);
$A^{39}$ is Asn or Cys(Psu);
$A^{40}$ is Ile or Cys(Psu);
$A''$ is Thr;
$A^{42}$ is Gln; and
$A^{43}$ is deleted;
or a pharmaceutical salt thereof.

5. A compound according to claim 2, wherein: $A^{43}$ is deleted; $A^2$ is 4Hppa; and at least one of $A_3$, $A_7$, $A^{11}$, $A^{13}$ and $A^{14}$ is not the amino acid residue of the corresponding position of native GIP; or a pharmaceutical salt thereof.

6. A compound according to claim 2, wherein: $A^2$ to $A^5$ and $A^{31}$ to $A^{43}$ are deleted; and at least one of $A^6$, $A^7$, $A^{11}$ and $A^{14}$ is not the amino acid residue of the corresponding position of native GIP; or a pharmaceutical salt thereof.

7. A compound according to claim 2, wherein: $A^2$ to $A^7$ and $A^{43}$ are deleted; and at least one of $A^8$ and $A^{31}$ is not the amino acid residue of the corresponding position of native GIP; or a pharmaceutical salt thereof.

8. A compound according to claim 2, wherein: $A^2$ to $A^5$ and $A^{43}$ are deleted; and at least one of $A^6$, $A^7$ and $A^{31}$ is not the amino acid residue of the corresponding position of native GIP; or a pharmaceutical salt thereof.

9. A compound according to claim 2, wherein: $A^2$ to $A^5$ and $A^{32}$ to $A^{43}$ are deleted; and at least one of $A^6$, $A^7$ and $A^{31}$ is not the amino acid residue of the corresponding position of native GIP; or a pharmaceutical salt thereof.

10. A compound according to claim 2, wherein said compound is:

(Ac-A6c⁷, Gln⁴³)hGIP(7-43)-OH;   (SEQ ID NO: 29)

or a pharmaceutically acceptable salt thereof.

11. A compound according to claim 3 or claim 4, further comprising a covalently linked PEG moiety, or a pharmaceutically acceptable salt thereof, wherein said PEG moiety is selected from the group consisting of 5K PEG, 10K PEG, 20K PEG, 30K PEG, 40K PEG, 50K PEG, and 60K PEG, to form Cys(succinimide-N-5K PEG), Cys(succinimide-N-10K PEG), Cys(succinimide-N-20K PEG), Cys(succinimide-N-30K PEG), Cys(succinimide-N-40K PEG), Cys(succinimide-N-50K PEG), Cys(succinimide-N-60K PEG), hCys(succinimide-N-5K PEG), hCys(succinimide-N-10K PEG), hCys(succinimide-N-20K PEG), hCys(succinimide-N-30K PEG), hCys(succinimide-N-40K PEG), hCys(succinimide-N-50K PEG), hCys(succinimide-N-60K PEG), Pen(succinimide-N-5K PEG), Pen(succinimide-N-10K PEG), Pen(succinimide-N-20K PEG), Pen(succinimide-N-30K PEG), Pen(succinimide-N-40K PEG), or Pen(succinimide-N-50K PEG), Pen(succinimide-N-60K PEG), or a pharmaceutically acceptable salt thereof.

12. A pharmaceutical composition comprising an effective amount of a compound of claim 1.

13. A method for treating conditions or diseases mediated by GIP-receptor binding, comprising the step of administering to a subject in need thereof a therapeutically effective amount of a compound of claim 1, wherein said condition or disease is selected from the group consisting of type 1 diabetes, type 2 diabetes, obesity, insulin resistance, glucose intolerance, fatty liver, glucagonomas, secretory disorders of the airway, metabolic disorders, arthritis, osteoporosis, central nervous system disease, restenosis, neurodegenerative disease, renal failure, congestive heart failure, nephrotic syndrome, cirrhosis, pulmonary edema, hypertension, and disorders wherein the reduction of food intake and/or losing body weight is desired.

14. The method of claim 13, wherein said diabetes is type 2 diabetes.

15. A method of treating diabetes-related disorders, comprising the step of administering to a subject in need thereof a therapeutically effective amount of a compound of claim 1, wherein said diabetes-related disorder is selected from the group consisting of hyperglycemia, hyperinsulinemia, impaired glucose tolerance, impaired fasting glucose, dyslipidemia, hypertriglyceridemia, and insulin resistance.

16. A method of stimulating insulin secretion in a subject in need thereof by administering to said subject a therapeutically effective amount of a compound of claim 1.

* * * * *

SEQUENCE LISTING

```
<160> NUMBER OF SEQ ID NOS: 50

<210> SEQ ID NO 1
<211> LENGTH: 42
<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 2
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 2

Tyr Ala Glu Gly Thr Phe Ile Ser Asp Tyr Ser Ile Ala Met Asp Lys
1               5                   10                  15
```

Ile His Gln Gln Asp Phe Val Asn Trp Leu Leu Ala Gln Lys
            20                  25                  30

<210> SEQ ID NO 3
<211> LENGTH: 42
<212> TYPE: PRT
<213> ORGANISM: Artificial sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid

<400> SEQUENCE: 3

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 4
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)

<400> SEQUENCE: 4

Xaa Ser Asp Tyr Ser Ile Ala Met Asp Lys Ile His Gln Gln Asp Phe
1               5                   10                  15

Val Asn Trp Leu Leu Ala Gln Lys Gly Lys Lys Asn Asp Trp Lys His
            20                  25                  30

Asn Ile Thr Gln
        35

<210> SEQ ID NO 5
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (34)..(34)
<223> OTHER INFORMATION: modified with N-propylsuccinimide (Psu)

<400> SEQUENCE: 5

```
Xaa Ser Asp Tyr Ser Ile Ala Met Asp Lys Ile His Gln Gln Asp Phe
1               5                   10                  15

Val Asn Trp Leu Leu Ala Gln Lys Gly Lys Asn Asp Trp Lys His
            20                  25                  30

Asn Cys Thr Gln
        35

<210> SEQ ID NO 6
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (33)..(33)
<223> OTHER INFORMATION: modified with N-propylsuccinimide (Psu)

<400> SEQUENCE: 6

Xaa Ser Asp Tyr Ser Ile Ala Met Asp Lys Ile His Gln Gln Asp Phe
1               5                   10                  15

Val Asn Trp Leu Leu Ala Gln Lys Gly Lys Asn Asp Trp Lys His
            20                  25                  30

Cys Ile Thr Gln
        35

<210> SEQ ID NO 7
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (32)..(32)
<223> OTHER INFORMATION: modified with N-propylsuccinimide (Psu)

<400> SEQUENCE: 7

Xaa Ser Asp Tyr Ser Ile Ala Met Asp Lys Ile His Gln Gln Asp Phe
1               5                   10                  15

Val Asn Trp Leu Leu Ala Gln Lys Gly Lys Asn Asp Trp Lys Cys
            20                  25                  30

Asn Ile Thr Gln
        35

<210> SEQ ID NO 8
<211> LENGTH: 36
<212> TYPE: PRT
<213> ORGANISM: Artificial Sequence
```

```
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (30)..(30)
<223> OTHER INFORMATION: modified with N-propylsuccinimide (Psu)

<400> SEQUENCE: 8

Xaa Ser Asp Tyr Ser Ile Ala Met Asp Lys Ile His Gln Gln Asp Phe
1               5                   10                  15

Val Asn Trp Leu Leu Ala Gln Lys Gly Lys Lys Asn Asp Cys Lys His
            20                  25                  30

Asn Ile Thr Gln
            35

<210> SEQ ID NO 9
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (29)..(29)
<223> OTHER INFORMATION: modified with N-propylsuccinimide (Psu)

<400> SEQUENCE: 9

Xaa Ser Asp Tyr Ser Ile Ala Met Asp Lys Ile His Gln Gln Asp Phe
1               5                   10                  15

Val Asn Trp Leu Leu Ala Gln Lys Gly Lys Lys Asn Cys Trp Lys His
            20                  25                  30

Asn Ile Thr Gln
            35

<210> SEQ ID NO 10
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
```

```
-continued

<222> LOCATION: (28)..(28)
<223> OTHER INFORMATION: modified with N-propylsuccinimide (Psu)

<400> SEQUENCE: 10

Xaa Ser Asp Tyr Ser Ile Ala Met Asp Lys Ile His Gln Gln Asp Phe
1               5                   10                  15

Val Asn Trp Leu Leu Ala Gln Lys Gly Lys Lys Cys Asp Trp Lys His
            20                  25                  30

Asn Ile Thr Gln
            35

<210> SEQ ID NO 11
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (27)..(27)
<223> OTHER INFORMATION: modified with N-propylsuccinimide (Psu)

<400> SEQUENCE: 11

Xaa Ser Asp Tyr Ser Ile Ala Met Asp Lys Ile His Gln Gln Asp Phe
1               5                   10                  15

Val Asn Trp Leu Leu Ala Gln Lys Gly Lys Cys Asn Asp Trp Lys His
            20                  25                  30

Asn Ile Thr Gln
            35

<210> SEQ ID NO 12
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (26)..(26)
<223> OTHER INFORMATION: modified with N-propylsuccinimide (Psu)

<400> SEQUENCE: 12

Xaa Ser Asp Tyr Ser Ile Ala Met Asp Lys Ile His Gln Gln Asp Phe
1               5                   10                  15

Val Asn Trp Leu Leu Ala Gln Lys Gly Cys Lys Asn Asp Trp Lys His
            20                  25                  30

Asn Ile Thr Gln
            35
```

```
<210> SEQ ID NO 13
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (25)..(25)
<223> OTHER INFORMATION: modified with N-propylsuccinimide (Psu)

<400> SEQUENCE: 13

Xaa Ser Asp Tyr Ser Ile Ala Met Asp Lys Ile His Gln Gln Asp Phe
1               5                   10                  15

Val Asn Trp Leu Leu Ala Gln Lys Cys Lys Lys Asn Asp Trp Lys His
            20                  25                  30

Asn Ile Thr Gln
        35

<210> SEQ ID NO 14
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (31)..(31)
<223> OTHER INFORMATION: modified with N-propylsuccinimide (Psu)

<400> SEQUENCE: 14

Xaa Ser Asp Tyr Ser Ile Ala Met Asp Lys Ile His Gln Gln Asp Phe
1               5                   10                  15

Val Asn Trp Leu Leu Ala Gln Lys Gly Lys Lys Asn Asp Trp Cys His
            20                  25                  30

Asn Ile Thr Gln
        35

<210> SEQ ID NO 15
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
```

```
<222> LOCATION: (1)..(1)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (25)..(25)
<223> OTHER INFORMATION: Xaa = ornithine (Orn)
<220> FEATURE:
<221> NAME/KEY: MOD_RES
<222> LOCATION: (25)..(25)
<223> OTHER INFORMATION: modified with (N-C(O)-(CH2)12-CH3)

<400> SEQUENCE: 15

Xaa Ser Asp Tyr Ser Ile Ala Met Asp Lys Ile His Gln Gln Asp Phe
1               5                   10                  15

Val Asn Trp Leu Leu Ala Gln Lys Xaa Lys Lys Asn Asp Trp Lys His
            20                  25                  30

Asn Ile Thr Gln
        35

<210> SEQ ID NO 16
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (25)..(25)
<223> OTHER INFORMATION: Xaa = ornithine (Orn)
<220> FEATURE:
<221> NAME/KEY: MOD_RES
<222> LOCATION: (25)..(25)
<223> OTHER INFORMATION: modified with (N-C(O)-(CH2)8-CH3)

<400> SEQUENCE: 16

Xaa Ser Asp Tyr Ser Ile Ala Met Asp Lys Ile His Gln Gln Asp Phe
1               5                   10                  15

Val Asn Trp Leu Leu Ala Gln Lys Xaa Lys Lys Asn Asp Trp Lys His
            20                  25                  30

Asn Ile Thr Gln
        35

<210> SEQ ID NO 17
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (25)..(25)
<223> OTHER INFORMATION: Xaa = ornithine
      (Orn)
<220> FEATURE:
<221> NAME/KEY: MOD_RES
```

<222> LOCATION: (25)..(25)
<223> OTHER INFORMATION: modified with (N-C(O)-(CH2)8-CH3)

<400> SEQUENCE: 17

Xaa Ser Asp Tyr Ser Ile Ala Met Asp Lys Ile His Gln Gln Asp Phe
1               5                   10                  15

Val Asn Trp Leu Leu Ala Gln Lys Xaa Lys Lys Asn Asp Trp Lys His
            20                  25                  30

Asn Ile Thr Gln
        35

<210> SEQ ID NO 18
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: modified with CH3-(CH2)8-C(O)
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (25)..(25)
<223> OTHER INFORMATION: Xaa = ornithine (Orn)
<220> FEATURE:
<221> NAME/KEY: MOD_RES
<222> LOCATION: (25)..(25)
<223> OTHER INFORMATION: modified with (N-C(O)-(CH2)8-CH3)

<400> SEQUENCE: 18

Xaa Ser Asp Tyr Ser Ile Ala Met Asp Lys Ile His Gln Gln Asp Phe
1               5                   10                  15

Val Asn Trp Leu Leu Ala Gln Lys Xaa Lys Lys Asn Asp Trp Lys His
            20                  25                  30

Asn Ile Thr Gln
        35

<210> SEQ ID NO 19
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (25)..(25)
<223> OTHER INFORMATION: Xaa = ornithine (Orn)
<220> FEATURE:
<221> NAME/KEY: MOD_RES
<222> LOCATION: (25)..(25)
<223> OTHER INFORMATION: modified with (N-C(O)-(CH2)4-CH3)

<400> SEQUENCE: 19

Xaa Ser Asp Tyr Ser Ile Ala Met Asp Lys Ile His Gln Gln Asp Phe

```
                1               5                  10                  15
Val Asn Trp Leu Leu Ala Gln Lys Xaa Lys Lys Asn Asp Trp Lys His
                20                  25                  30

Asn Ile Thr Gln
        35

<210> SEQ ID NO 20
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (25)..(25)
<223> OTHER INFORMATION: Xaa = ornithine (Orn)
<220> FEATURE:
<221> NAME/KEY: MOD_RES
<222> LOCATION: (25)..(25)
<223> OTHER INFORMATION: modified with (N-C(O)-(CH2)4-CH3)

<400> SEQUENCE: 20

Xaa Ser Asp Tyr Ser Ile Ala Met Asp Lys Ile His Gln Gln Asp Phe
1               5                  10                  15

Val Asn Trp Leu Leu Ala Gln Lys Xaa Lys Lys Asn Asp Trp Lys His
                20                  25                  30

Asn Ile Thr Gln
        35

<210> SEQ ID NO 21
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: modified with CH3-(CH2)4-C(O)
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (25)..(25)
<223> OTHER INFORMATION: Xaa = ornithine (Orn)
<220> FEATURE:
<221> NAME/KEY: MOD_RES
<222> LOCATION: (25)..(25)
<223> OTHER INFORMATION: modified with (N-C(O)-(CH2)4-CH3)

<400> SEQUENCE: 21

Xaa Ser Asp Tyr Ser Ile Ala Met Asp Lys Ile His Gln Gln Asp Phe
1               5                  10                  15

Val Asn Trp Leu Leu Ala Gln Lys Xaa Lys Lys Asn Asp Trp Lys His
                20                  25                  30

Asn Ile Thr Gln
        35

<210> SEQ ID NO 22
```

```
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (28)..(28)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: modified with (N-C(O)-(CH2)8-CH3)

<400> SEQUENCE: 22

Xaa Ser Asp Tyr Ser Ile Ala Met Asp Lys Ile His Gln Gln Asp Phe
1               5                   10                  15

Val Asn Trp Leu Leu Ala Gln Lys Gly Lys Lys Xaa Asp Trp Lys His
            20                  25                  30

Asn Ile Thr Gln
        35

<210> SEQ ID NO 23
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (28)..(28)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: modified with (N-C(O)-(CH2)8-CH3)

<400> SEQUENCE: 23

Xaa Ser Asp Tyr Ser Ile Ala Met Asp Lys Ile His Gln Gln Asp Phe
1               5                   10                  15

Val Asn Trp Leu Leu Ala Gln Lys Gly Lys Lys Xaa Asp Trp Lys His
            20                  25                  30

Asn Ile Thr Gln
        35

<210> SEQ ID NO 24
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: modified with CH3-(CH2)8-C(O)
```

```
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (28)..(28)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: modified with (N-C(O)-(CH2)8-CH3)

<400> SEQUENCE: 24

Xaa Ser Asp Tyr Ser Ile Ala Met Asp Lys Ile His Gln Gln Asp Phe
1               5                   10                  15

Val Asn Trp Leu Leu Ala Gln Lys Gly Lys Lys Xaa Asp Trp Lys His
            20                  25                  30

Asn Ile Thr Gln
        35

<210> SEQ ID NO 25
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (25)..(25)
<223> OTHER INFORMATION: modified with N-hexylsuccinimide (Hsu)

<400> SEQUENCE: 25

Xaa Ser Asp Tyr Ser Ile Ala Met Asp Lys Ile His Gln Gln Asp Phe
1               5                   10                  15

Val Asn Trp Leu Leu Ala Gln Lys Cys Lys Lys Asn Asp Trp Lys His
            20                  25                  30

Asn Ile Thr Gln
        35

<210> SEQ ID NO 26
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (25)..(25)
<223> OTHER INFORMATION: modified with N-hexylsuccinimide (Hsu)

<400> SEQUENCE: 26

Xaa Ser Asp Tyr Ser Ile Ala Met Asp Lys Ile His Gln Gln Asp Phe
1               5                   10                  15
```

Val Asn Trp Leu Leu Ala Gln Lys Cys Lys Lys Asn Asp Trp Lys His
            20                  25                  30

Asn Ile Thr Gln
        35

<210> SEQ ID NO 27
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (25)..(25)
<223> OTHER INFORMATION: Xaa = beta-(2-naphthyl)alanine (2Nal)

<400> SEQUENCE: 27

Xaa Ser Asp Tyr Ser Ile Ala Met Asp Lys Ile His Gln Gln Asp Phe
1               5                   10                  15

Val Asn Trp Leu Leu Ala Gln Lys Xaa Lys Lys Asn Asp Trp Lys His
            20                  25                  30

Asn Ile Thr Gln
        35

<210> SEQ ID NO 28
<211> LENGTH: 40
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 4-hydroxyproline (4Hyp)
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c)

<400> SEQUENCE: 28

Xaa Gly Thr Phe Xaa Ser Asp Tyr Ser Ile Ala Met Asp Lys Ile His
1               5                   10                  15

Gln Gln Asp Phe Val Asn Trp Leu Leu Ala Gln Lys Gly Lys Lys Asn
            20                  25                  30

Asp Trp Lys His Asn Ile Thr Gln
            35                  40

<210> SEQ ID NO 29
<211> LENGTH: 37
<212> TYPE: PRT
<213> ORGANISM: Artificial Sequence
<220> FEATURE:
<223> OTHER INFORMATION: Synthetic analog of glucose-dependent

```
    insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)

<400> SEQUENCE: 29

Xaa Ser Asp Tyr Ser Ile Ala Met Asp Lys Ile His Gln Gln Asp Phe
1               5                   10                  15

Val Asn Trp Leu Leu Ala Gln Lys Gly Lys Lys Asn Asp Trp Lys His
            20                  25                  30

Asn Ile Thr Gln Gln
        35

<210> SEQ ID NO 30
<211> LENGTH: 28
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (25)..(25)
<223> OTHER INFORMATION: modified with N-propylsuccinimide (Psu)
<220> FEATURE:
<221> NAME/KEY: MOD_RES
<222> LOCATION: (28)..(28)
<223> OTHER INFORMATION: AMIDATION

<400> SEQUENCE: 30

Xaa Ser Asp Tyr Ser Ile Ala Met Asp Lys Ile His Gln Gln Asp Phe
1               5                   10                  15

Val Asn Trp Leu Leu Ala Gln Lys Cys Lys Lys Asn
            20                  25

<210> SEQ ID NO 31
<211> LENGTH: 25
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (25)..(25)
<223> OTHER INFORMATION: modified with N-propylsuccinimide (Psu)
<220> FEATURE:
<221> NAME/KEY: MOD_RES
<222> LOCATION: (25)..(25)
```

<223> OTHER INFORMATION: AMIDATION

<400> SEQUENCE: 31

Xaa Ser Asp Tyr Ser Ile Ala Met Asp Lys Ile His Gln Gln Asp Phe
1               5                   10                  15

Val Asn Trp Leu Leu Ala Gln Lys Cys
            20                  25

<210> SEQ ID NO 32
<211> LENGTH: 37
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 1-amino-1-cyclohexanecarboxylic acid
      (A6c)
<220> FEATURE:
<221> NAME/KEY: MOD_RES
<222> LOCATION: (26)..(26)
<223> OTHER INFORMATION: modified with N-propylsuccinimide (Psu)

<400> SEQUENCE: 32

Phe Xaa Ser Asp Tyr Ser Ile Ala Met Asp Lys Ile His Gln Gln Asp
1               5                   10                  15

Phe Val Asn Trp Leu Leu Ala Gln Lys Cys Lys Lys Asn Asp Trp Lys
            20                  25                  30

His Asn Ile Thr Gln
        35

<210> SEQ ID NO 33
<211> LENGTH: 37
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = 1-amino-1-cyclohexanecarboxylic acid
      (A6c)
<220> FEATURE:
<221> NAME/KEY: MOD_RES
<222> LOCATION: (26)..(26)
<223> OTHER INFORMATION: modified with N-propylsuccinimide (Psu)

<400> SEQUENCE: 33

Phe Xaa Ser Asp Tyr Ser Ile Ala Met Asp Lys Ile His Gln Gln Asp
1               5                   10                  15

Phe Val Asn Trp Leu Leu Ala Gln Lys Cys Lys Lys Asn Asp Trp Lys
            20                  25                  30

His Asn Ile Thr Gln
        35

<210> SEQ ID NO 34
<211> LENGTH: 25
<212> TYPE: PRT
<213> ORGANISM: Artificial Sequence
<220> FEATURE:
<223> OTHER INFORMATION: Synthetic analog of glucose-dependent
      insulinotropic polypeptide (GIP)

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 1-amino-1-cyclohexanecarboxylic acid
      (A6c)
<220> FEATURE:
<221> NAME/KEY: MOD_RES
<222> LOCATION: (25)..(25)
<223> OTHER INFORMATION: AMIDATION

<400> SEQUENCE: 34

Phe Xaa Ser Asp Tyr Ser Ile Ala Met Asp Lys Ile His Gln Gln Asp
1               5                   10                  15

Phe Val Asn Trp Leu Leu Ala Gln Lys
            20                  25

<210> SEQ ID NO 35
<211> LENGTH: 26
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 1-amino-1-cyclohexanecarboxylic acid
      (A6c)
<220> FEATURE:
<221> NAME/KEY: MOD_RES
<222> LOCATION: (26)..(26)
<223> OTHER INFORMATION: modified with N-propylsuccinimide (Psu)
<220> FEATURE:
<221> NAME/KEY: MOD_RES
<222> LOCATION: (26)..(26)
<223> OTHER INFORMATION: AMIDATION

<400> SEQUENCE: 35

Phe Xaa Ser Asp Tyr Ser Ile Ala Met Asp Lys Ile His Gln Gln Asp
1               5                   10                  15

Phe Val Asn Trp Leu Leu Ala Gln Lys Cys
            20                  25

<210> SEQ ID NO 36
<211> LENGTH: 26
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = 1-amino-1-cyclohexanecarboxylic acid
      (A6c)
<220> FEATURE:
<221> NAME/KEY: MOD_RES
<222> LOCATION: (26)..(26)
<223> OTHER INFORMATION: modified with N-propylsuccinimide (Psu)
<220> FEATURE:
<221> NAME/KEY: MOD_RES
<222> LOCATION: (26)..(26)
<223> OTHER INFORMATION: AMIDATION

<400> SEQUENCE: 36
```

```
Phe Xaa Ser Asp Tyr Ser Ile Ala Met Asp Lys Ile His Gln Gln Asp
1               5                   10                  15

Phe Val Asn Trp Leu Leu Ala Gln Lys Cys
            20                  25

<210> SEQ ID NO 37
<211> LENGTH: 25
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
      (A5c)
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (25)..(25)
<223> OTHER INFORMATION: AMIDATION

<400> SEQUENCE: 37

Phe Xaa Ser Asp Tyr Ser Ile Ala Xaa Asp Lys Ile His Gln Gln Asp
1               5                   10                  15

Phe Val Asn Trp Leu Leu Ala Gln Lys
            20                  25

<210> SEQ ID NO 38
<211> LENGTH: 25
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = 1-amino-1-cyclohexanecarboxylic acid
      (A6c)
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (25)..(25)
<223> OTHER INFORMATION: AMIDATION

<400> SEQUENCE: 38

Phe Xaa Ser Asp Tyr Ser Ile Ala Xaa Asp Lys Ile His Gln Gln Asp
1               5                   10                  15

Phe Val Asn Trp Leu Leu Ala Gln Lys
            20                  25

<210> SEQ ID NO 39
<211> LENGTH: 25
<212> TYPE: PRT
<213> ORGANISM: Artificial Sequence
<220> FEATURE:
```

```
<223> OTHER INFORMATION: Synthetic analog of glucose-dependent
      insulinotropic polypeptide (GIP)
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (25)..(25)
<223> OTHER INFORMATION: AMIDATION

<400> SEQUENCE: 39

Phe Ile Ser Asp Tyr Xaa Ile Ala Xaa Asp Lys Ile His Gln Gln Asp
1               5                   10                  15

Phe Val Asn Trp Leu Leu Ala Gln Lys
            20                  25

<210> SEQ ID NO 40
<211> LENGTH: 34
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (25)..(25)
<223> OTHER INFORMATION: modified with N-propylsuccinimide (Psu)

<400> SEQUENCE: 40

Asp Tyr Ser Ile Ala Met Asp Lys Ile His Gln Gln Asp Phe Val Asn
1               5                   10                  15

Trp Leu Leu Ala Gln Lys Gly Lys Cys Asn Asp Trp Lys His Asn Ile
            20                  25                  30

Thr Gln

<210> SEQ ID NO 41
<211> LENGTH: 35
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (24)..(24)
<223> OTHER INFORMATION: Xaa = ornithine (Orn)
<220> FEATURE:
<221> NAME/KEY: MOD_RES
<222> LOCATION: (24)..(24)
<223> OTHER INFORMATION: modified with (N-C(O)-(CH2)8-CH3)

<400> SEQUENCE: 41

Ser Asp Tyr Ser Ile Ala Met Asp Lys Ile His Gln Gln Asp Phe Val
1               5                   10                  15
```

```
Asn Trp Leu Leu Ala Gln Lys Xaa Lys Lys Asn Asp Trp Lys His Asn
            20                  25                  30

Ile Thr Gln
        35

<210> SEQ ID NO 42
<211> LENGTH: 35
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: modified with cyclohexyl carboxylic acid (Chc)
<220> FEATURE:
<221> NAME/KEY: MOD_RES
<222> LOCATION: (24)..(24)
<223> OTHER INFORMATION: modified with N-propylsuccinimide (Psu)

<400> SEQUENCE: 42

Ser Asp Tyr Ser Ile Ala Met Asp Lys Ile His Gln Gln Asp Phe Val
1               5                   10                  15

Asn Trp Leu Leu Ala Gln Lys Cys Lys Lys Asn Asp Trp Lys His Asn
            20                  25                  30

Ile Thr Gln
        35

<210> SEQ ID NO 43
<211> LENGTH: 35
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: modified with CH3-(CH2)4-C(O)
<220> FEATURE:
<221> NAME/KEY: MOD_RES
<222> LOCATION: (24)..(24)
<223> OTHER INFORMATION: modified with N-propylsuccinimide (Psu)

<400> SEQUENCE: 43

Ser Asp Tyr Ser Ile Ala Met Asp Lys Ile His Gln Gln Asp Phe Val
1               5                   10                  15

Asn Trp Leu Leu Ala Gln Lys Cys Lys Lys Asn Asp Trp Lys His Asn
            20                  25                  30

Ile Thr Gln
        35

<210> SEQ ID NO 44
<211> LENGTH: 41
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (2)..(2)
<223> OTHER INFORMATION: Xaa = 4-hydroxyproline (4Hyp)
<220> FEATURE:
<221> NAME/KEY: MISC_FEATURE
```

```
<222> LOCATION: (6)..(6)
<223> OTHER INFORMATION: Xaa = 1-amino-1-cyclohexanecarboxylic acid
      (A6c)

<400> SEQUENCE: 44

Xaa Xaa Gly Thr Phe Xaa Ser Asp Tyr Ser Ile Ala Met Asp Lys Ile
1               5                   10                  15

His Gln Gln Asp Phe Val Asn Trp Leu Leu Ala Gln Lys Gly Lys Lys
            20                  25                  30

Asn Asp Trp Lys His Asn Ile Thr Gln
        35                  40

<210> SEQ ID NO 45
<211> LENGTH: 41
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (13)..(13)
<223> OTHER INFORMATION: Xaa = norleucine (Nle)

<400> SEQUENCE: 45

Xaa Pro Gly Thr Phe Ile Ser Asp Tyr Ser Ile Ala Xaa Asp Lys Ile
1               5                   10                  15

His Gln Gln Asp Phe Val Asn Trp Leu Leu Ala Gln Lys Gly Lys Lys
            20                  25                  30

Asn Asp Trp Lys His Asn Ile Thr Gln
        35                  40

<210> SEQ ID NO 46
<211> LENGTH: 41
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (12)..(12)
<223> OTHER INFORMATION: Xaa = alpha-aminoisobutyric acid (Aib)

<400> SEQUENCE: 46

Xaa Glu Gly Thr Phe Ile Ser Asp Tyr Ser Ile Xaa Met Asp Lys Ile
1               5                   10                  15

His Gln Gln Asp Phe Val Asn Trp Leu Leu Ala Gln Lys Gly Lys Lys
            20                  25                  30

Asn Asp Trp Lys His Asn Ile Thr Gln
        35                  40

<210> SEQ ID NO 47
<211> LENGTH: 41
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
```

```
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (13)..(13)
<223> OTHER INFORMATION: Xaa = 1-amino-1-cyclohexanecarboxylic acid
      (A6c)

<400> SEQUENCE: 47

Xaa Glu Gly Thr Phe Ile Ser Asp Tyr Ser Ile Ala Xaa Asp Lys Ile
1               5                   10                  15

His Gln Gln Asp Phe Val Asn Trp Leu Leu Ala Gln Lys Gly Lys Lys
            20                  25                  30

Asn Asp Trp Lys His Asn Ile Thr Gln
        35                  40

<210> SEQ ID NO 48
<211> LENGTH: 41
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (10)..(10)
<223> OTHER INFORMATION: Xaa = 1-amino-1-cyclohexanecarboxylic acid
      (A6c)

<400> SEQUENCE: 48

Xaa Glu Gly Thr Phe Ile Ser Asp Tyr Xaa Ile Ala Met Asp Lys Ile
1               5                   10                  15

His Gln Gln Asp Phe Val Asn Trp Leu Leu Ala Gln Lys Gly Lys Lys
            20                  25                  30

Asn Asp Trp Lys His Asn Ile Thr Gln
        35                  40

<210> SEQ ID NO 49
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (13)..(13)
<223> OTHER INFORMATION: Xaa = norleucine (Nle)
<220> FEATURE:
<221> NAME/KEY: MOD_RES
<222> LOCATION: (42)..(42)
<223> OTHER INFORMATION: modified with (N-C(O)-(CH2)10-CH3)

<400> SEQUENCE: 49

Xaa Glu Gly Thr Phe Ile Ser Asp Tyr Xaa Ile Ala Xaa Asp Lys Ile
1               5                   10                  15
```

```
His Gln Gln Asp Phe Val Asn Trp Leu Leu Ala Gln Lys Gly Lys Lys
                  20                  25                  30

Asn Asp Trp Lys His Asn Ile Thr Gln Lys
                35                  40

<210> SEQ ID NO 50
<211> LENGTH: 36
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c)
<220> FEATURE:
<221> NAME/KEY: MOD_RES
<222> LOCATION: (36)..(36)
<223> OTHER INFORMATION: AMIDATION

<400> SEQUENCE: 50

Xaa Ser Asp Tyr Ser Ile Ala Met Asp Lys Ile His Gln Gln Asp Phe
1               5                  10                  15

Val Asn Trp Leu Leu Ala Gln Lys Gly Lys Lys Asn Asp Trp Lys His
                20                  25                  30

Asn Ile Thr Gln
            35
```